US011684743B2

(12) United States Patent
Hocking et al.

(10) Patent No.: US 11,684,743 B2
(45) Date of Patent: Jun. 27, 2023

(54) YOKE FOR HEADGEAR

(71) Applicant: Fisher & Paykel Healthcare Limited, Auckland (NZ)

(72) Inventors: Jake Baker Hocking, Auckland (NZ); Priyanka Ferdinand Pereira, Auckland (NZ); Bruce Michael Walls, Auckland (NZ)

(73) Assignee: FISHER & PAYKEL HEALTHCARE LIMITED, Auckland (NZ)

(*) Notice: Subject to any disclaimer, the term of this patent is extended or adjusted under 35 U.S.C. 154(b) by 981 days.

(21) Appl. No.: 16/335,635

(22) PCT Filed: Sep. 28, 2017

(86) PCT No.: PCT/NZ2017/050126
§ 371 (c)(1),
(2) Date: Mar. 21, 2019

(87) PCT Pub. No.: WO2018/063009
PCT Pub. Date: Apr. 5, 2018

(65) Prior Publication Data
US 2019/0217039 A1 Jul. 18, 2019

Related U.S. Application Data

(60) Provisional application No. 62/401,063, filed on Sep. 28, 2016.

(51) Int. Cl.
*A61M 16/06* (2006.01)

(52) U.S. Cl.
CPC .... *A61M 16/0683* (2013.01); *A61M 16/0616* (2014.02); *A61M 2205/0216* (2013.01)

(58) Field of Classification Search
CPC .......... A61M 16/0683; A61M 16/0688; A61M 16/0694; A61M 16/0605; A61M 16/0611;
(Continued)

(56) References Cited

U.S. PATENT DOCUMENTS 3,917,757 A 11/1975 Hoag
5,588,423 A 12/1996 Smith
(Continued)

FOREIGN PATENT DOCUMENTS

AU 2015264928 12/2015
CA 2151992 6/1996
(Continued)

OTHER PUBLICATIONS

International Search Report, International Searching Authority, Application No. PCT/NZ2017/050126, dated Nov. 22, 2017, in 9 pages.

*Primary Examiner* — Joseph D. Boecker
*Assistant Examiner* — Brian T Khong
(74) *Attorney, Agent, or Firm* — Knobbe, Martens, Olson & Bear, LLP

(57) ABSTRACT

The apparatus, method, and system disclosed relates to a headgear assembly for a respiratory system for the delivery of respiratory therapy to a patient. The headgear comprises a yoke at least partially formed from an elastomeric material. The yoke is configured to be stretched under tension to attach the yoke to the headgear assembly.

20 Claims, 27 Drawing Sheets

(58) Field of Classification Search
CPC .......... A61M 16/0616; A61M 16/0622; A61M 16/0627; A61M 16/06; A61M 16/0633; A61M 16/0638; A61M 16/0644; A61M 16/065; A61M 16/0655; A61M 2016/0661; A61M 2205/0216

See application file for complete search history.

(56) References Cited

U.S. PATENT DOCUMENTS

| | | | |
|---|---|---|---|
| 5,971,369 | A | 10/1999 | Neveu et al. |
| 6,149,141 | A | 11/2000 | Birdsell et al. |
| 6,435,180 | B1 | 8/2002 | Hewson et al. |
| 6,812,435 | B2 | 11/2004 | Schilling |
| 7,096,864 | B1 | 8/2006 | Mayer et al. |
| 7,111,624 | B2 | 9/2006 | Thudor et al. |
| 8,443,807 | B2* | 5/2013 | McAuley ........ A61M 16/0825 128/207.18 |
| 2003/0111080 | A1* | 6/2003 | Olsen ............. A61M 16/0666 128/207.11 |
| 2004/0045909 | A1 | 3/2004 | Tomioka et al. |
| 2005/0205395 | A1 | 9/2005 | Dietrich et al. |
| 2007/0193582 | A1 | 8/2007 | Kwok et al. |
| 2012/0138061 | A1* | 6/2012 | Dravitzki ....... A61M 16/0611 128/205.25 |
| 2013/0152937 | A1* | 6/2013 | Jablonski ....... A61M 16/0683 128/205.25 |
| 2013/0186404 | A1* | 7/2013 | Chien ............. A61M 16/0825 128/206.21 |
| 2014/0276177 | A1* | 9/2014 | Brambilla ....... A61M 16/06 128/201.13 |
| 2014/0345621 | A1* | 11/2014 | Zack .............. A61M 16/06 29/428 |
| 2015/0224274 | A1* | 8/2015 | Siew ............. A61M 16/0622 128/206.24 |
| 2016/0144146 | A1* | 5/2016 | Huddart ......... A61M 16/0816 128/206.21 |

FOREIGN PATENT DOCUMENTS

| | | |
|---|---|---|
| WO | WO 00/012197 | 3/2000 |
| WO | WO 04/043528 | 5/2004 |
| WO | WO 04/112873 | 12/2004 |
| WO | WO 06/107818 | 10/2006 |
| WO | WO 07/019625 | 2/2007 |
| WO | WO 08/024001 | 2/2008 |
| WO | WO 2008/056993 | 5/2008 |
| WO | WO 2009/108995 | 9/2009 |
| WO | WO 2010/135785 | 12/2010 |
| WO | WO 2013/042004 | 3/2013 |
| WO | WO 2014/015382 | 1/2014 |
| WO | WO 2014/110626 | 7/2014 |
| WO | WO 2014/175752 | 10/2014 |
| WO | WO 2016/043603 | 3/2016 |
| WO | WO 07/045017 | 4/2017 |
| WO | WO 2017/160166 | 9/2017 |

\* cited by examiner

YOKE FOR HEADGEAR

BACKGROUND

Technical Field

The present disclosure generally relates to a respiratory system for the delivery of respiratory therapy to a patient. More particularly, the present disclosure relates to a yoke and a headgear assembly for use in a respiratory system.

Description of the Related Art

Respiratory masks are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnoea (OSA), a condition in which a patient's airway intermittently collapses during sleep, preventing the patient from breathing for a period of time. The cessation of breathing, or apnoea, results in the patient awakening. Repetitive and frequent apnoeas may result in the patient rarely achieving a full and restorative night's sleep.

CPAP therapy involves the delivery of a supply of continuous positive air pressure to the airway of the patient via a respiratory mask. The continuous positive pressure acts as a splint within the patient's airway, which secures the airway in an open position such that the patient's breathing and sleep are not interrupted.

Respiratory masks typically comprise a patient interface and a headgear, wherein the patient interface is configured to deliver the supply of continuous positive air pressure to the patient's airway via a cushion module, typically comprising a seal and frame assembly. The seal of the cushion module is configured to form an airtight seal in or around the patient's nose and/or mouth. Respiratory masks are available in a range of styles including full-face, nasal, direct nasal and oral masks, which create an airtight seal with the nose and/or mouth. The cushion module is held in place on the patient's face by the headgear. In order to maintain an airtight seal, the headgear should provide support to the patient interface such that it is held in a stable position relative to the patient's face during use. Such respiratory masks may also be used to deliver NIV and other therapies.

A yoke can be used to form a connection point between headgear and a cushion module, as shown in FIG. 1. The yoke comprises a middle region located between two distal ends, each of which is typically attached to a free end of a front strap of the headgear. Headgear that comprises a yoke may be commonly referred to as closed loop headgear because the rear strap, front straps, and yoke of the headgear connect together to form a closed loop. The shape and width of the yoke determines the position of the ends of the yoke (and connection to front straps of the headgear) relative to the patient's face. If the yoke is too flat and wide, a moment arm may result, which reduces the stability of the cushion module on a patient's face, as shown in FIG. 2. This problem may be exacerbated if a patient has a small head or a particularly narrow face. To overcome this problem, the yoke may be curved so that ends of the yoke are positioned closer to the patient's face, as shown in FIG. 3. However, if the yoke is too curved, the ends may dig into the patient's cheeks, particularly when patient movement applies a rotational force to the yoke, as shown by dashed lines in FIG. 3. The ends of the yoke may also dig into the patient's cheeks if the yoke ends have a large head or a substantially flat facial profile.

BRIEF SUMMARY

The systems and devices described herein have innovative aspects, no single one of which is indispensable or solely responsible for their desirable attributes. Without limiting the scope of the claims, some of the advantageous features will now be summarized.

In a first aspect, the invention provides a headgear assembly for a patient interface of a respiratory system, wherein the headgear comprises at least one strap to wrap around a user's head and a yoke connected to ends of the at least one strap, wherein the yoke is at least partially formed from an elastomeric material and wherein the yoke comprises at least one engagement member configured to attach to at least one retention member of the patient interface.

Preferably, the headgear comprises a rear strap connected to a pair of front straps, and wherein the yoke comprises a middle region located between two side regions that terminate at distal ends of the yoke, and wherein the distal ends of the yoke are configured to connect to free ends of the front straps.

Optionally, the yoke is fully formed from an elastomeric material.

In one form, the yoke comprises an upper surface, a lower surface, a front surface and a rear surface, and wherein a pair of stepped regions are provided on the upper surface and/or lower surface and/or rear surface of the yoke, each stepped region separating the middle region from each side region. Optionally, each stepped region comprises a transitional wall separating the middle region from the side regions, wherein each transitional wall forms an abutment surface configured to align with a corresponding abutment surface within a channel of a frame of a patient interface. Preferably, the abutment surfaces face toward each other and are angled outwardly toward distal ends of the yoke.

In one form, the side regions of the yoke are substantially rigid.

Optionally, each side region of the yoke comprises a washer box housing. In one form, the yoke comprises at least one collection chamber to receive one or more filaments from an automatically adjustable headgear system In one form, the yoke comprises distal ends and each distal end is connected to a headgear connector assembly comprising a washer box housing and a connector configured to connect to a front strap of the headgear.

In another form, the yoke comprises distal ends and each distal end is connected to a connector configured to connect to a front strap of the headgear.

Optionally, the yoke comprises substantially rounded edges.

In one form, the engagement member of the yoke comprises an aperture and the retention member comprises an arm configured to be received within the aperture.

In a second aspect, the invention provides a respiratory system comprising a patient interface comprising a mask assembly and a headgear assembly of any one of the preceding claims.

In one form, the mask assembly comprises a seal and frame assembly, and wherein the frame comprises a front surface and a rear surface, the front surface of the frame comprising a yoke channel extending laterally across the frame, the yoke channel being configured to receive the yoke of the headgear assembly.

Optionally, the yoke channel comprises an upper surface, a lower surface and a rear surface, wherein edges of the upper and lower surfaces each form a lip to define the front opening of the channel, and wherein the lips of the channel project toward each other so that the maximum distance between the lips is less than the maximum distance between the upper and lower surfaces of the channel.

In one form, the upper and lower surfaces of the channel are substantially concave along at least a portion of the length of the channel to provide the channel with a substantially C-shaped cross-section.

Preferably, the yoke channel comprises one or more retention members configured to retain the yoke within the channel.

Optionally, each retention feature comprises a tab that at least partially projects across the yoke channel and in front of the yoke when the yoke is located within the channel.

In one form, the mask assembly comprises a frame comprising a front surface and a rear surface, and wherein one or more retention members project from the front surface of the frame for engagement with one or more engagement members of the yoke.

Optionally, the mask assembly comprises a frame comprising a pair of arms projecting from left and right sides of the frame and the yoke comprises at least a pair of apertures, and wherein the distance between the apertures is less than the distance between the arms.

In one form, each yoke aperture provides access to a pocket or loop provided on the yoke and each arm is configured to pass through a respective yoke aperture to engage with the pocket or loop.

In a third aspect, the invention provides a method of attaching a yoke to a patient interface, the method comprising the steps of: engaging a first engagement member of the yoke, located at or near a first end of the yoke, with a first retention member located on a first side of the patient interface to hold the yoke to the patient interface at a first anchor point; pulling the yoke against the first anchor point until a second engagement member, located at or near a second end of the yoke, substantially aligns with a second retention member located on a second side of the patient interface; engaging the second retention member with the second engagement member as the yoke is held under tension; and releasing the yoke.

Also disclosed herein is a headgear assembly for a respiratory system. The headgear comprises a rear strap connected to a pair of front straps and a yoke that is at least partially formed from an elastomeric material. The yoke comprises a middle region, located between two side regions that terminate at distal ends of the yoke. The distal ends of the yoke are configured to connect to free ends of the front straps of the headgear.

In one form, the yoke is fully formed from an elastomeric material.

In one form, the yoke comprises an upper surface, a lower surface, a front surface and a rear surface. A pair of stepped regions may be provided on the upper surface and/or lower surface and/or rear surface of the yoke, each stepped region separating the middle region from a side region. In one form, each stepped region comprises a transitional wall separating the middle region from the side regions. The transitional wall forms an abutment surface configured to align with a corresponding abutment surface within a channel of a frame of a patient interface. Optionally, the abutment surfaces are angled toward each other in a direction from the front surface of the yoke to the rear surface.

In one form, the side regions of the yoke are substantially rigid.

Preferably, each side region of the yoke comprises a washer box housing. In this form, the yoke may comprise at least one collection chamber for receiving one or more filaments from an automatically adjustable headgear system In one form, each distal end of the yoke is connected to a headgear connector assembly comprising a washer box housing and a strap connector configured to connect to a front strap of the headgear. Alternatively, each distal end of the yoke is connected to a connector configured to connect to a front strap of the headgear.

In one form, the yoke may comprise substantially rounded edges. In this form, the yoke may be configured to engage with a frame having a yoke channel comprising a substantially C-shaped lateral cross-section.

Also disclosed herein is a respiratory system comprising a patient interface comprising a cushion module and a headgear assembly of the first aspect of the invention.

In one form, the cushion module comprises a seal and frame assembly. The frame may comprise a front surface and a rear surface, the front surface of the frame comprising a yoke channel extending laterally across the frame. The yoke channel may be configured to receive the yoke of the headgear assembly.

In one form, the yoke channel comprises an upper surface, a lower surface and a rear surface. Edges of the upper and lower surfaces may each form a lip to define the front opening of the channel. The lips of the channel may project toward each other so that the distance between the lips is less than the maximum distance between the upper and lower surfaces of the channel. Optionally, the upper and lower surfaces of the channel are substantially concave along at least a portion of the length of the channel to provide the channel with a substantially 'C-shaped' cross-section.

In one form, the yoke channel comprises a plurality of retention features configured to retain the yoke within the channel. Each retention feature may optionally comprise a tab that at least partially projects across the yoke channel and in front of the yoke when the yoke is located within the channel.

Also disclosed herein is a respiratory mask system comprising a frame as disclosed herein and a yoke as disclosed herein. The frame and yoke may comprise any feature or combination of features as described herein.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made.

Terms such as "top", "bottom", "upper", "lower", "front", "back", "left", "right", "rear", and "side" describe the orientation and/or location of portions of the components or elements within a consistent but arbitrary frame of reference which is made clear by reference to the text and the associated drawings describing the components or elements under discussion. Moreover, terms such as "first", "second", "third", and so on may be used to describe separate components. Such terminology may include the words specifically mentioned above, derivatives thereof, and words of similar import.

DETAILED DESCRIPTION

Referring to FIGS. 4 to 29, the invention relates to a respiratory mask system 1000 for the delivery of respiratory therapy to a patient. The mask system 1000 may comprise a patient interface 2000 and may also comprise a headgear assembly 3000. The headgear assembly 3000 may comprise an elastomeric yoke 100, by which to attach the headgear 3000 to the patient interface 2000. The yoke 100 may be integrally formed with one or more straps of the headgear 3000 or the yoke may be detachably connected to one or more straps of the headgear.

In one form, the patient interface 2000 comprises a seal and frame assembly. The seal 2100 may comprise a front or distal surface 2110 and a rear surface or proximal surface 2120. The rear surface 2120 of the seal 2100 may be configured to substantially seal against a patient's face during use. The seal 2100 may be configured to fit over a patient's mouth, nose, or both. In one form, the seal 2100 comprises nasal pillows that substantially seal around a patient's nares. In another form, the patient interface 2000 is a non-sealing interface such as a nasal cannula configured for high flow therapy.

The frame 2200 of the patient interface 2000 may be configured to attach the patient interface 2000 to the headgear 3000. In one form, as shown in FIGS. 1, 4, 5, and 13, the frame 2200 comprises a body 2210 comprising a first surface or front surface 2211 and a substantially opposing second surface or rear surface 2212. The frame 2200 may also comprise a gas inlet 2220 configured to attach to a gas conduit 4000 for delivering a gas to the patient via the patient interface 1000. Optionally, the frame 2200 may also comprise one or more outlet vents 2230. The elastomeric yoke 100 is typically configured to attach headgear 3000 to the frame 2200.

In one form, the front surface 2211 of the frame comprises a yoke channel 210 configured to receive at least a portion of a yoke of a headgear assembly 3000 therein. The yoke channel 210 may extend across at least a portion of the front surface 2211 of the frame 2200 from left to right.

Figure 1:
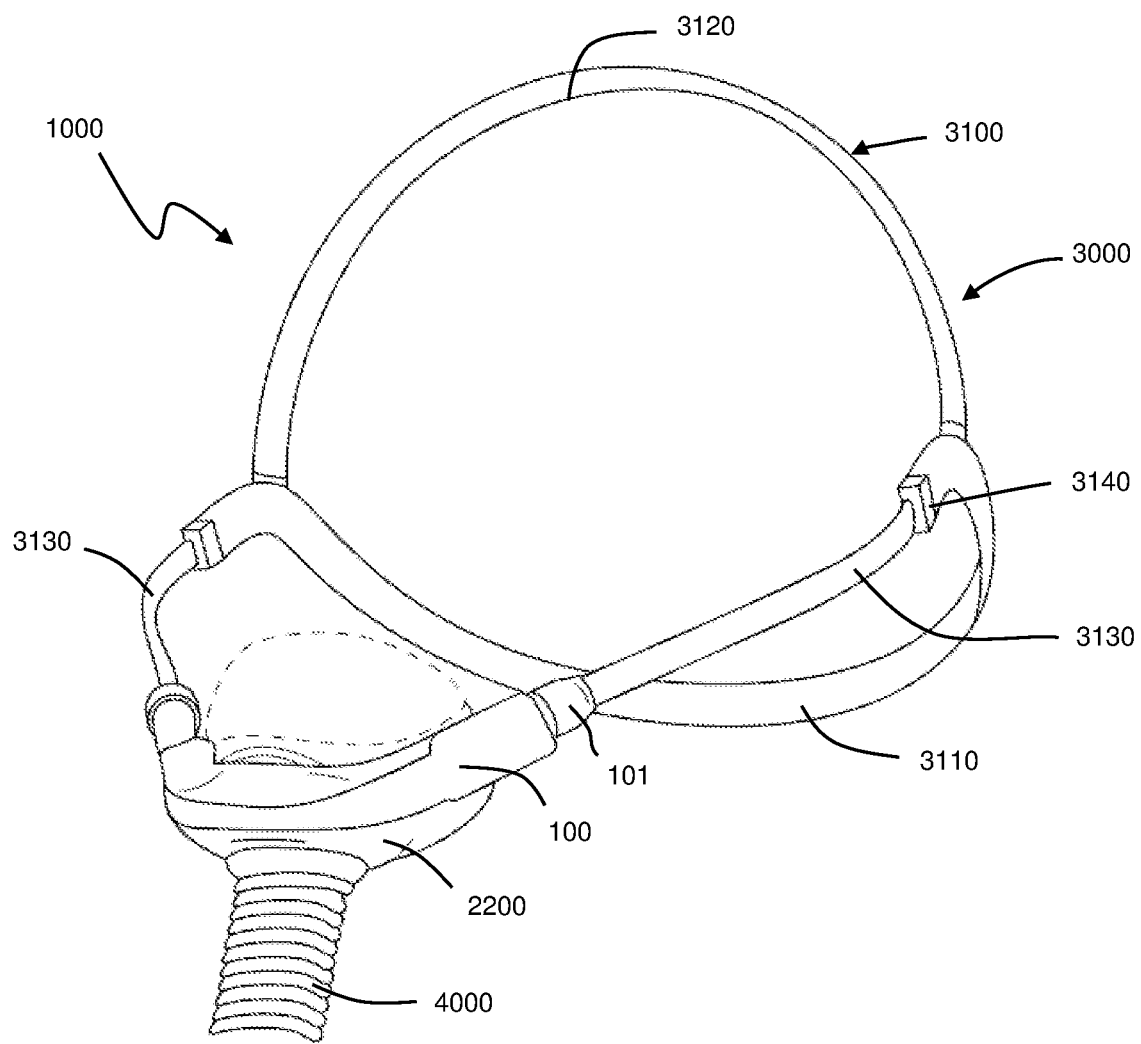
FIG. 1 is a perspective view of a mask assembly, including a headgear assembly with yoke, a seal assembly, and a frame assembly.
Figure 3:
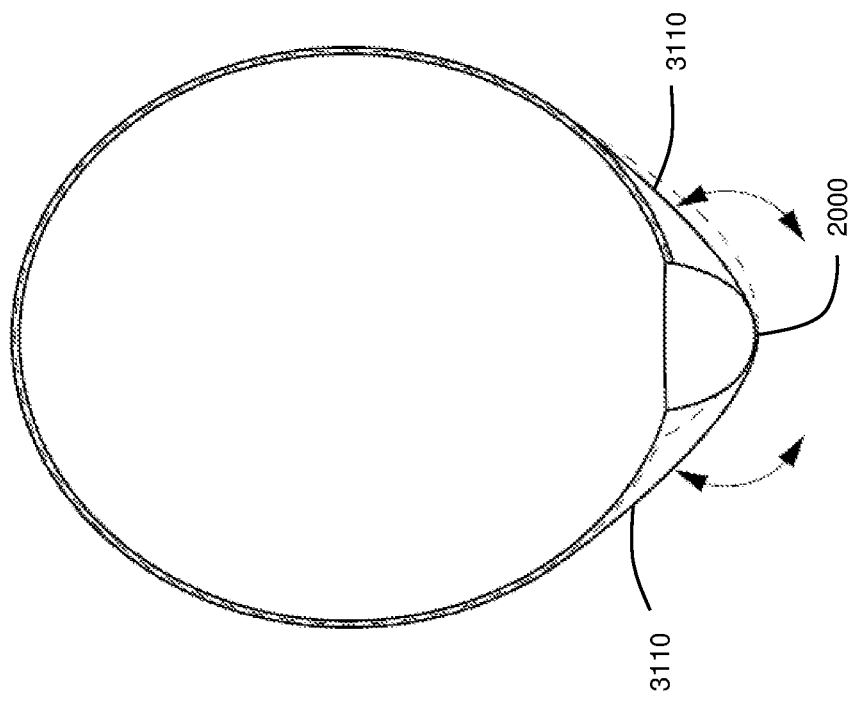
FIG. 3 is another schematic plan view of a patient interface illustrating how an ill-fitting yoke may shift in relation to a patient's face.
Figure 2:
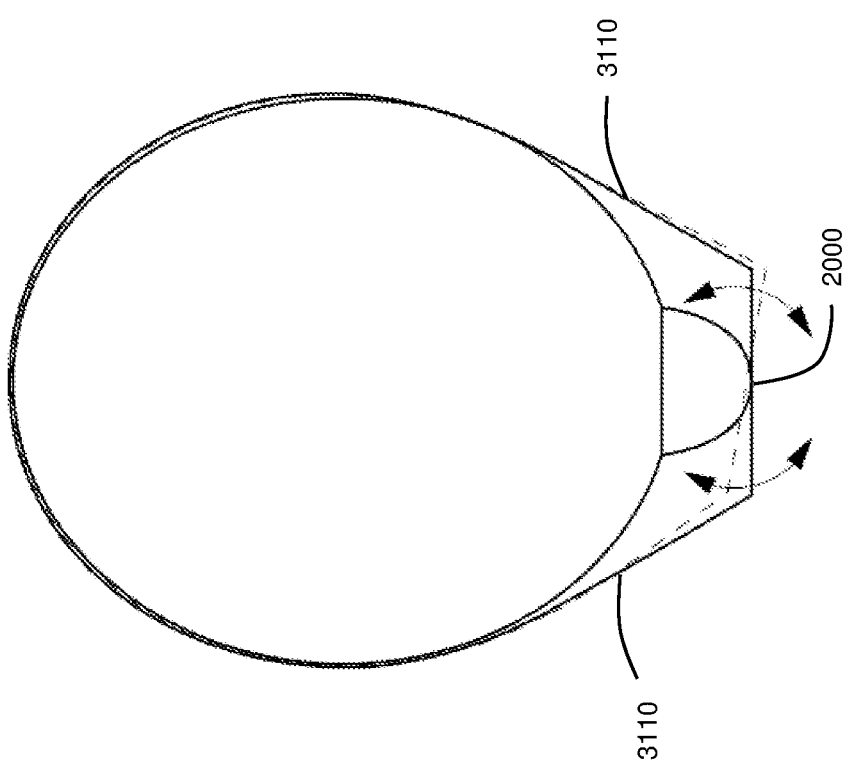
FIG. 2 is a schematic plan view of a patient interface comprising a yoke to connect headgear to a cushion module of the interface and illustrating how an ill-fitting yoke may shift in relation to a patient's face.
Figure 4:
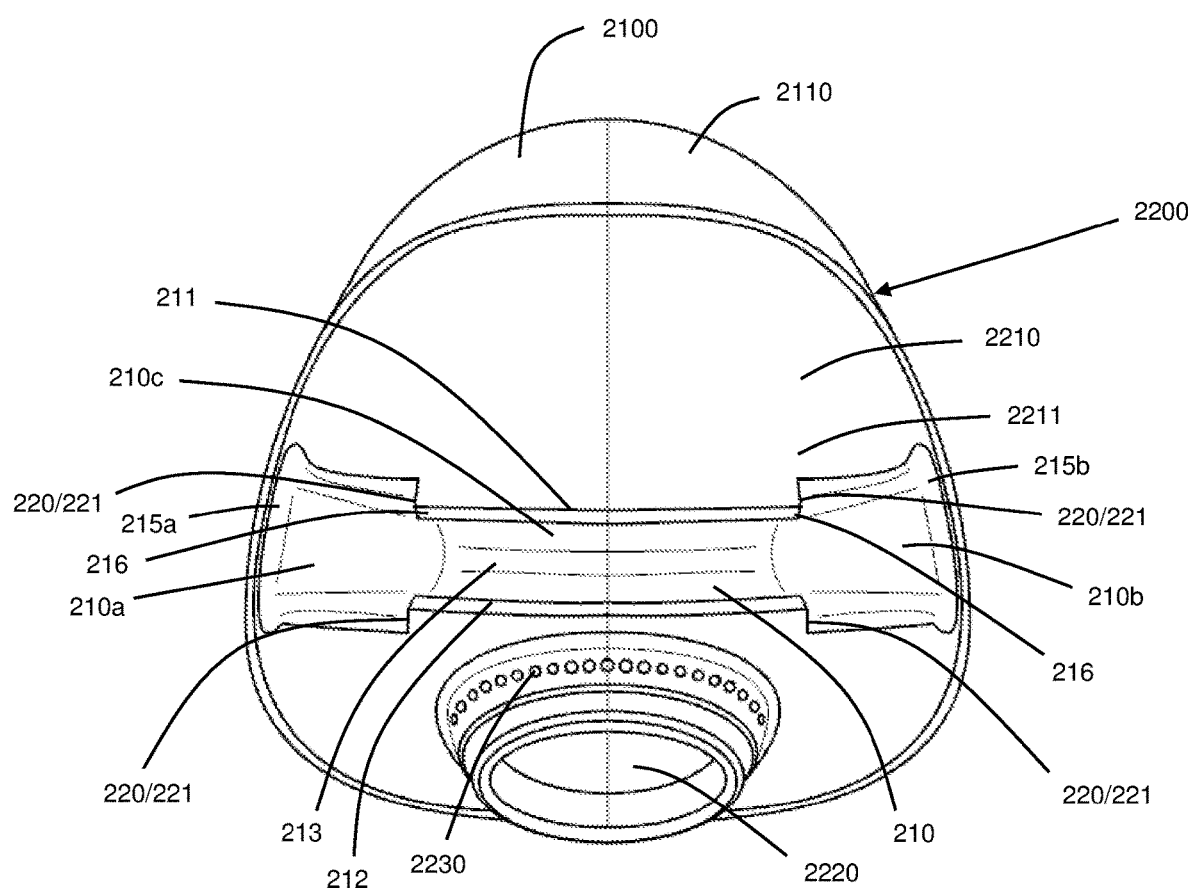
FIG. 4 is a front view of one form of frame with a yoke channel.
Figure 5:
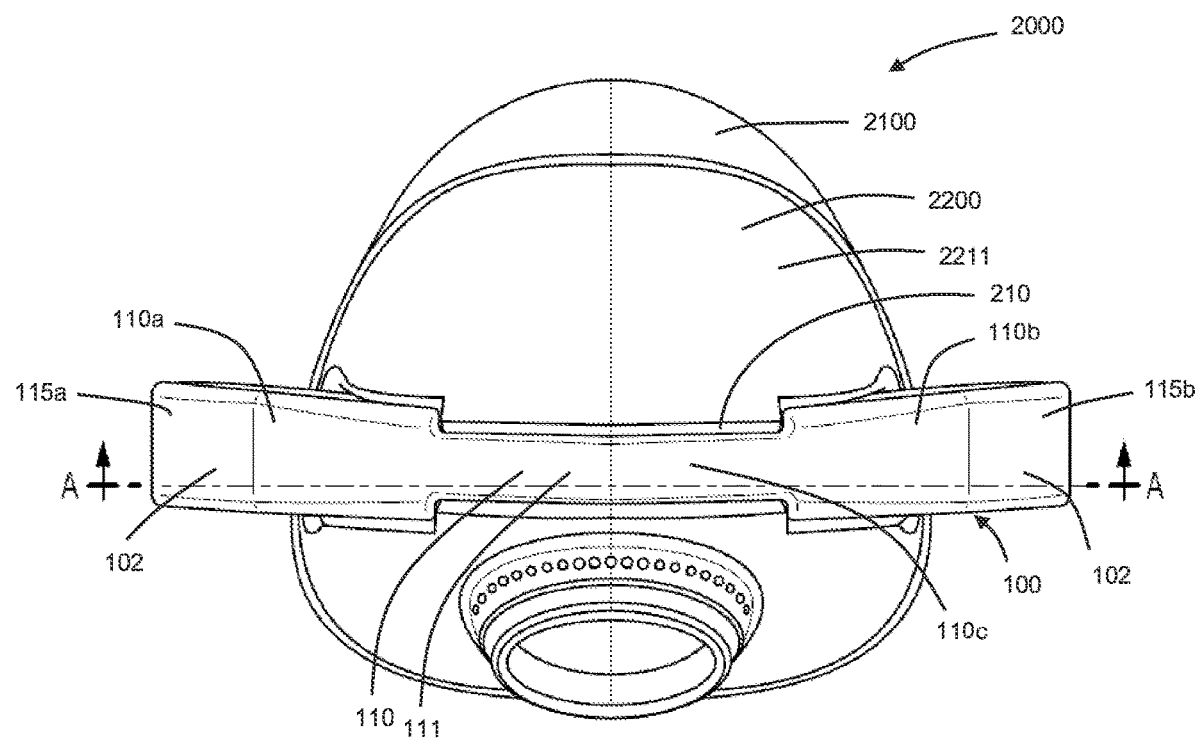
FIG. 5 is a front view of the frame of FIG. 4 with a yoke connected within the yoke channel.
Figure 10:
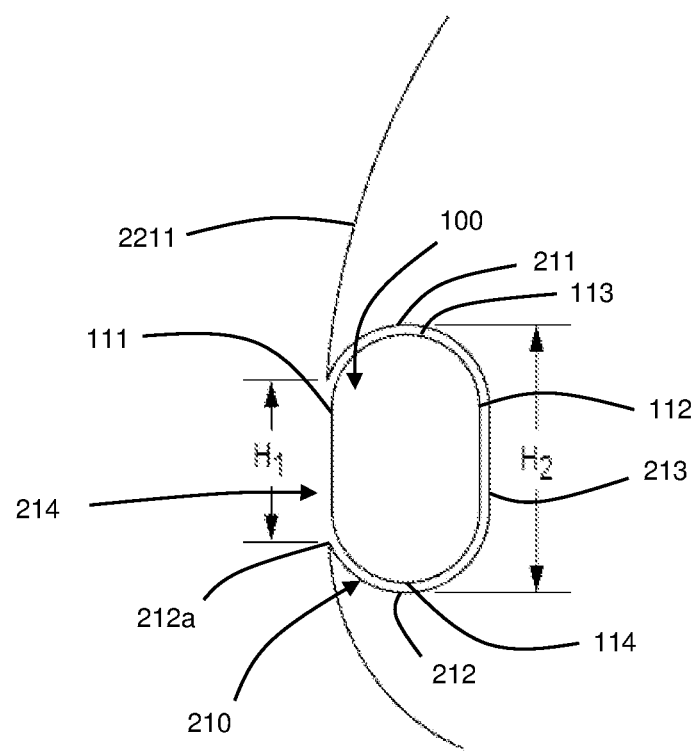
FIG. 10 is a schematic cross-sectional side view of one form of yoke channel having a substantially 'C-shaped' cross-section to receive a yoke having rounded edges, as shown in FIG. 7.

As shown in FIGS. 4, 5 and 10, the yoke channel 210 may be defined by a first wall 211, forming an upper surface when in use, a second wall 212, forming a lower surface that substantially opposes the first wall 211, and a third wall 213 forming a rear surface that extends between the first and second walls 211, 212. The channel 210 may comprise two side regions 210a, 210b, each side region being located at an opposite end of the channel 210, and a middle region 210c located substantially centrally between the two side regions 210a, 210b.

In one form, the height $H_2$ of the rear surface 213 of the channel 210 may be substantially defined by the distance between the upper and lower walls 211, 212 of the channel 210. At its middle region 210c, the maximum height of the channel 210 may be less than the maximum height of the channel 210 at one or both side regions 210a, 210b. For example, the upper or lower surface 211, 212 of the channel 210 may curve or angle toward the opposing surface 212, 211 to form a peak substantially located at a central point along the length of the channel 210.

In one form, as shown in FIG. 10, the maximum height $H_1$ of the front opening 214 of the yoke channel 210 (i.e. the distance between opposing edges of the channel at the front surface of the frame) may be less than the maximum height $H_2$ between the upper and lower walls 211, 212 within the interior of the yoke channel 210. For example, the height $H_1$ of the channel opening 214 may be less than the height $H_2$ of the rear surface 213 of the channel 210. In some forms, the maximum height $H_1$ of the channel opening 214 is less than the maximum height $H_2$ of the interior of the channel 210 in a middle region 210c of the channel only.

In one form, the lower surface 212 of the yoke channel 210 may angle inwardly toward the rear surface 213 of the channel.

In one form, the upper surface 211 of the yoke channel may angle inwardly toward the rear surface 213 of the channel 210.

In one form, the lower surface 212 of the yoke channel 210 may have a depth substantially defined by the distance between the rear surface 213 of the channel and a front edge 212a of the lower surface 212, where the lower surface 212 meets the front surface 2211 of the frame 2200. In one form, the depth of the lower surface 212 of the yoke channel may be greater at areas adjacent to retention members 220 or abutment surfaces 221 (that hold the yoke within the yoke channel) than at lateral ends of the middle region 210c of the channel or than at the side regions 210a, 210b or ends 215a, 215b of the channel 210. In another form, the depth of the lower surface 212 may taper towards the ends of the yoke channel 210.

In one form, the depth of the lower surface 212 tapers from a first depth adjacent to abutment surfaces 221 of the yoke channel 210 to a second depth at the lateral ends 215a, 215b of the yoke channel 210.

The frame 2200 and yoke channel 210 may be substantially curved from left to right to conform to some extent to the curves around a patient's nose or mouth. Alternatively, or additionally, the frame 2200 and/or yoke channel 210 may slope or curve downwardly, from top to bottom, toward the seal or patient's face, or away from the seal or patient's face.

The headgear assembly 3000 of the respiratory mask system 1000 is used to hold the patient interface 2000 to the patient's face. The headgear assembly 3000 is typically attached to the patient interface 2000 and wraps tightly around the rear of the patient's head to seal the patient interface 2000 against the patient's face.

The headgear assembly 1000 may comprise an elastomeric yoke or collector 100, which is configured to attach the headgear 3000 to the frame 2100 of the patient interface 2000, as best shown in FIGS. 1, 5 to 13, 15 to 18, 20A to 20C, 21, and 24 to 29. The yoke is configured to be stretched under tension to attach the yoke to the headgear assembly.

The elastomeric yoke 100 may be stretchable and/or flexible and may also be configured to attach to straps 3100 of the headgear assembly 3000. In the embodiment shown in FIG. 1, the headgear assembly 3000 comprises an assembly of straps 3100, including a rear strap 3110 configured to wrap behind a patient's head, an upper strap 3120 configured to wrap over the top of a patient's head, and a pair of front straps 3130 configured to extend along the patient's cheeks during use. In one form, each front strap 3130 is attached to the rear strap 3110 of the headgear assembly 3000 by rear connectors 3140. In another form, the rear strap 3110 comprises side extensions that form front straps 3130 to extend along the patient's cheeks during use.

Each front strap 3130 may comprise a free end to which may be attached a connector 3140. Each connector 3140 may engage with a complementary strap connector 101 located on the yoke 100. The connection between the front straps 3130 and yoke 100 may be any suitable form of connection, such as a snap-fit connection, a screw and thread type connection, or a hooked connection. FIGS. 1, 5 to 13, 15 to 18, 20A to 20C, 21, and 24 to 29 illustrate various forms of elastomeric yoke 100 that may be used to attach a headgear assembly 3000 to a frame 2200. The yoke 100 comprises a substantially elongate body 110 having distal ends 115a, 115b that may be configured to connect to headgear straps. For example, a strap connector 101 may be located at or near each end of the yoke 100.

Figure 6:
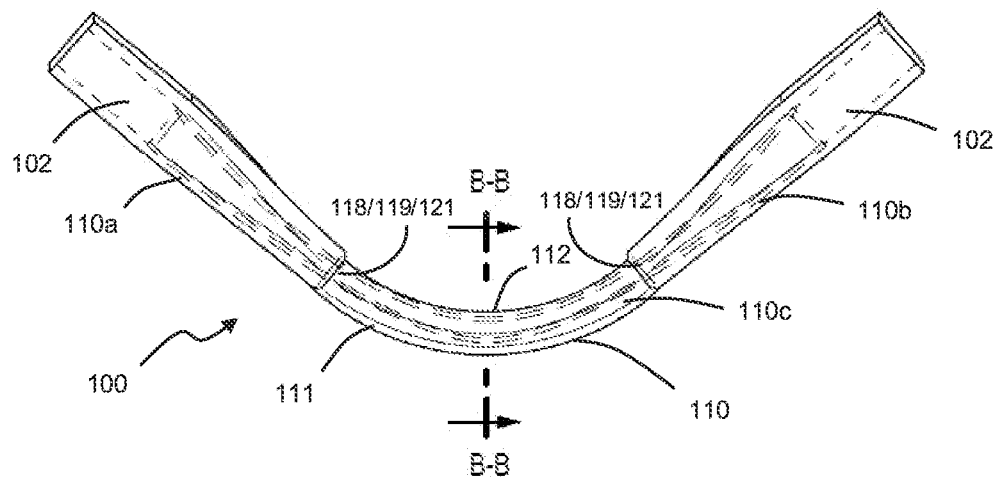
FIG. 6 is a top view of one form of yoke having a stepped region on its upper, rear, and lower surfaces and showing hidden detail, including a washer box housing and a pair of hollow collection chambers within the body of the yoke.
Figure 6A:
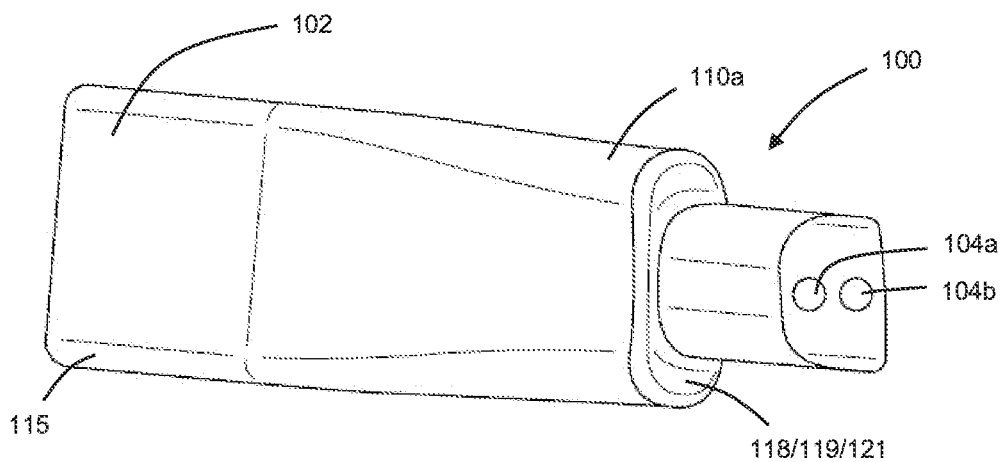
FIG. 6A is a cross-sectional side view taken along line B-B of the yoke of FIG. 6 and showing the tubular-like collection chambers within the yoke.

The elastomeric yoke 100 may be configured to attach any suitable headgear assembly 3000 to the frame 2200. For example, in some forms, as shown in FIGS. 6 and 6A, the yoke 100 may form a collector for filaments used in an automatically adjustable headgear system 3000, such as those described in WO 2016/043603 and PCT/NZ20141000074 which are incorporated herein by reference. In this form, each side region of the yoke 100 may comprise a housing 102 or washer box comprising a washer mechanism (which may also be referred to as a directional lock) for the automatically adjustable headgear system The washer mechanism/directional lock may be configured to frictionally engage with a filament during elongation of the headgear, but to also allow relatively friction-free movement during retraction of the headgear 3000. The washer box/directional lock housing 102 may comprise a substantially hollow recess formed in a side region of the yoke/collector 100 to receive the directional lock and filaments of the automatically adjustable headgear system 3000 within the yoke body 110.

FIGS. 30A to 30D show one form of an automatically adjustable headgear system comprising a directional lock/washer mechanism within a housing/washer box, a first and a second lock element (e.g., washer 1820, 1822) and a filament/core member 1830. The directional lock housing comprises a first and a second chamber 1840, 1842 wherein the first and second chambers 1840, 1842 are configured to house the first and second lock washers 1820, 1822, respectively. In the illustrated arrangement, the first and second chambers 1840, 1842 are separated by an internal wall 1812 of the housing 1810. However, in other arrangements, the first and second chambers 1840, 1842 are not necessarily physically separate spaces, but can be portions of a chamber. The directional lock housing 1810 comprises two end walls 1814, which along with the internal wall 1812, have an elongate core opening/hollow recess 1860 for the filament/core member 1830 to pass through. The core openings 1860 are substantially aligned with each other. The core opening 1860 of the end wall 1814 shown on the right side of the figures is larger than the core opening of the internal wall 1812 and the end wall 1814 shown on the left of the figures. This allows for manipulation of the path of the filament/core member 1830 through the housing 1810. The first and second chambers 1840, 1842 are each delimited by the internal wall 1812, one of the end walls 1814 and a pair of side walls 1816; wherein the side walls 1816 extend between the end walls 1814 of the housing 1810. The first and second chambers 1840, 1842 are configured to be open at one or both of a top and a bottom of the housing 1810.

Each of the first and second chambers 1840, 1842 has a pair of washer retainers 1850 that are aligned on opposing side walls 1816 of the housing 1810. Each pair of washer retainers 1850 is configured to pivotally retain one of the first or second lock washers 1820, 1822 within the respective first or second chamber 1840, 1842. The washer retainers comprise a circular bush 1852 and an elongate slot 1854, wherein circular bushes 1852 intersect with the bottom of the housing such that an entrance is formed. The entrance is configured to allow the first and/or second lock washers 1820, 1822 to be received into the washer retainers 1850. The slot 1854 extends radially from the circular bush 1852 towards the top of the housing 1810.

The first and second washers 1820, 1822 comprise a cylindrical shaft 1824 and an arm 1826 that extends from the shaft 1824. The cylindrical shaft 1824 is substantially the same width W, as the housing 1810 and the arm 1826 is narrower to fit within the first and second chambers 1840, 1842. In the illustrated arrangement, the arm 1826 comprises a first section 1872 and a second section 1874, wherein the first section 1872 extends radially or perpendicularly from the cylindrical shaft 1824 and the second section 1874 extends at an obtuse angle from the end of the first section 1872. The first section 1872 of the arm 1826 of the first washer 1820 is shorter than the first section 1872 of the arm 1826 of the second washer 1822. The angle between the first and second sections 1872, 1874 of the arm 1826 of the first washer 1820 is greater than the corresponding angle of the second washer 1822. The angles can be selected such that the second section 1874 of one or both of the first and second washers 1820, 1822 lies substantially flat against the corresponding wall (e.g., internal wall 1812 and end wall 1814, respectively) of the housing 1810 in one position of the washers 1820, 1822. The second section 1874 of the arm 1826 comprises a centrally located circular aperture 1876 configured to receive the core member 1830. The first and second chambers 1840, 1842 differ in size according to the size of the washer that is to be housed within it, i.e. the first chamber 1840 is smaller than the second chamber 1842 because the first washer 1820 is smaller than the second washer 1822.

The cylindrical shafts 1824 of the first and second lock washers 1820, 1822 have a diameter substantially the same as that of the circular bushes 1852 of the washer retainer 1850, and are configured to be received and retained by the circular bush 1852 in a snap-fit configuration. The snap-fit configuration is provided by the entrance of the circular bush 1852 being narrower than the diameter of the cylindrical shaft 1824. The slots 1854 of the washer retainers 1850 are configured to allow the entrance to be flexed open to increase the ease with which the first and second lock washers 1820, 1822 can be pushed through the entrances and assembled to the housing 1810. Once assembled within the first and second chambers 1840, 1842 of the housing 1810, the first and second washers 1820, 1822 can pivot back and forward around a central axis that runs through the cylindrical shaft 1824.

Figure 30A:
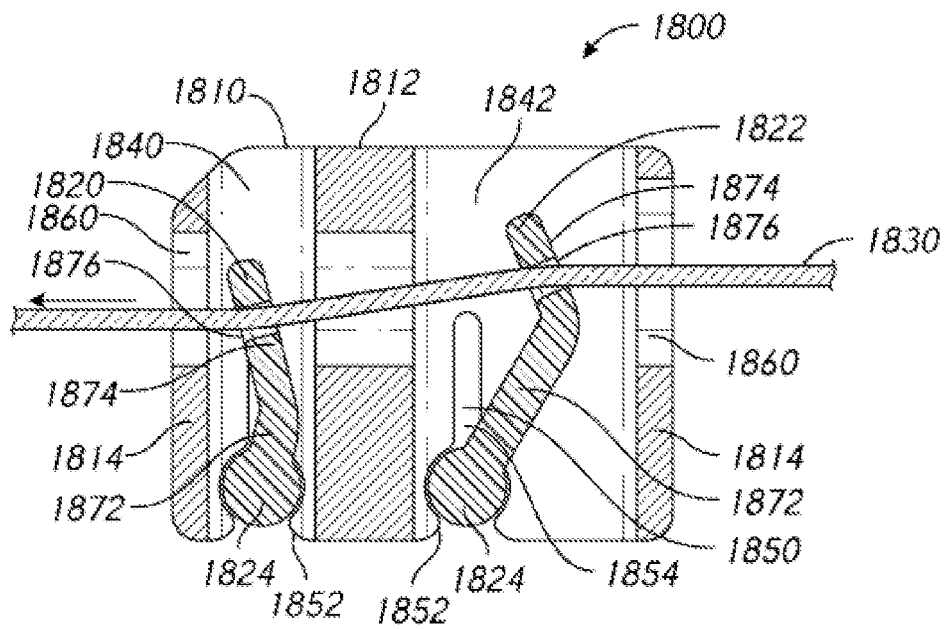
FIGS. 30A to 30D are cross-sectional views of a washer box/directional lock housing of an adjustable headgear assembly showing directional locks in a locked configuration (FIGS. 30A and 30B) and an open configuration (FIGS. 30C and 30D).
Figure 30B:
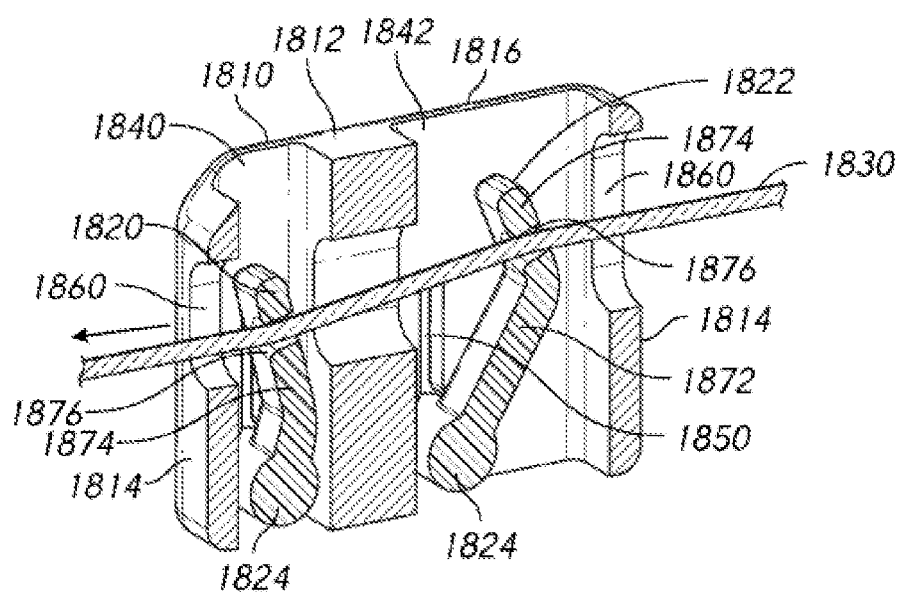
Figure 30C:
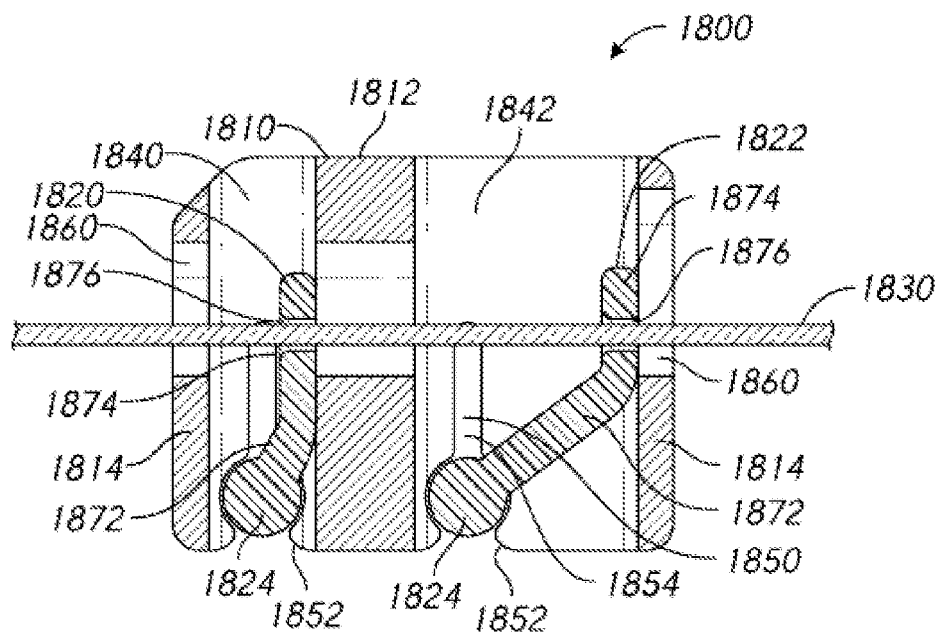
Figure 30D:
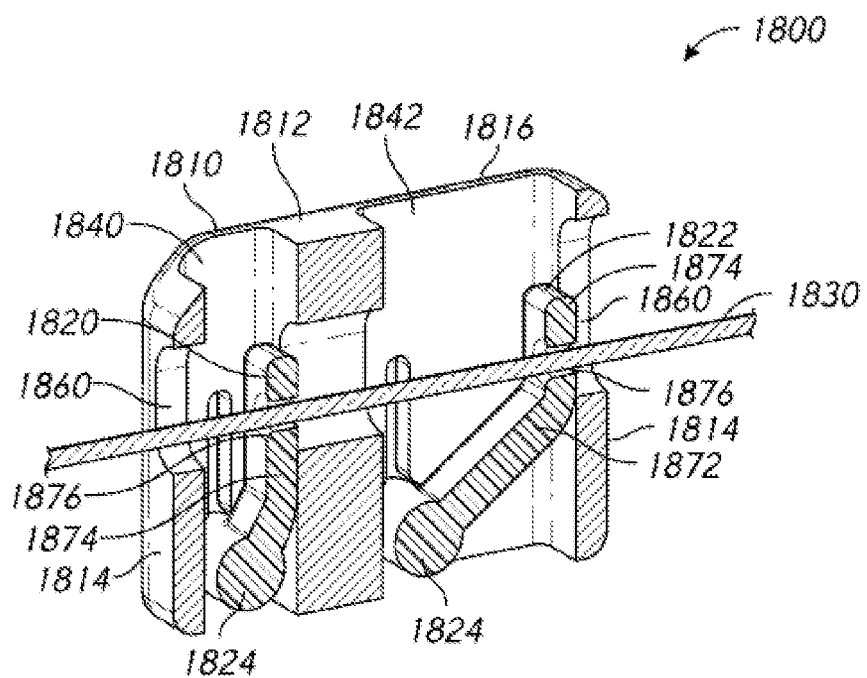

The filament/core member 1830 is configured to pass through the core openings 1860 of the housing 1810 and the apertures 1876 of the first and second washers 1820, 1822. Application of a tension force to the core member 1830 causes the first and second lock washers 1820, 1822 to pivot back and/or forward between a locked position and/or open position. FIGS. 30A and 30B show the directional lock in a locked configuration in which a force is applied to the core member 1830 in a direction towards the left side of the figure (as indicated by the arrow). The force applied to the core member 1830 in this configuration causes the first and second lock washers 1820, 1822 to pivot in an anti-clockwise direction, such that the path of the core member 1830 through the directional lock 1800 is non-linear or tortuous and movement of the core member 1830 is restricted. FIGS. 30C and 30D show the directional lock in an open configuration in which a force is applied to the core member 1830 in a direction towards the right side of the figure (as indicated by the arrow). In this configuration, the first and second lock washers 1820, 1822 are pivoted in a clockwise direction such that the circular apertures 1876 and core openings 1860 are aligned in a substantially straight line. This provides a smooth path for the core member 1830 to be pulled substantially freely through the directional lock 1800.

Optionally, the yoke 100 comprises at least one hollow collection chamber 104 for receiving at least one filament/core member of the adjustable headgear system 1000. The hollow collection chamber 104 may open into and extend between the washer box housings 102. For example, each hollow collection chamber typically aligns and connects with a respective core opening 1860 of the washer box/directional lock housing to form a pathway for a filament/core member 1830 so that a filament/core member 1830 can extend through a core opening 1860 and through a collection chamber in the yoke. In one form, as shown in FIG. 6A, the yoke 100 may comprise two hollow collection chambers 104a, 104b, where each collection chamber is configured to receive a filament of the adjustable headgear system 1000 so as not to interfere with the filament or washer box of the other adjustment mechanism of the headgear. In one form, as shown in FIG. 6A, each collection chamber 104a, 104b comprises a hollow tube in which to receive a filament. The tube(s) may be over-moulded into the yoke 100 when the yoke is manufactured.

In another form, each end of the yoke 100 may be attached to a strap connector 101 or to a connector assembly comprising both a washer box housing 102 and a strap connector 101 configured to attach the yoke 100 to headgear 3000. In this form, the washer box housings 102 and/or connectors 101 may be made separately from the yoke 100 and may be configured to attach to the ends of the yoke in any suitable arrangement, such as a snap-fit arrangement, or by overmoulding for example.

Figure 7:
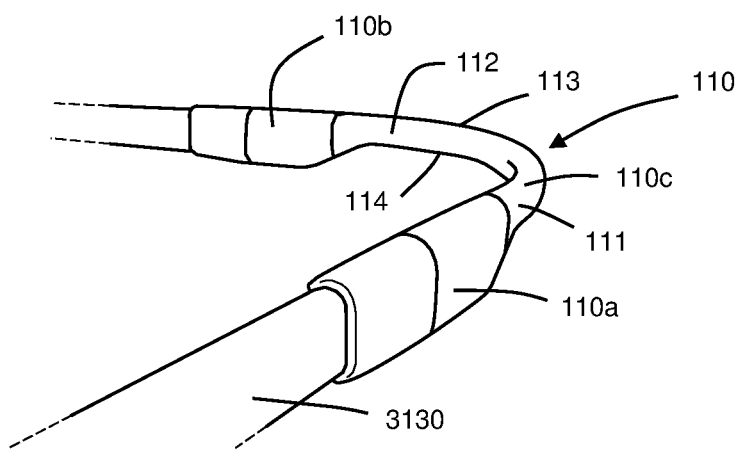
FIG. 7 is a rear perspective view of one form of yoke with a connector assembly attached.
Figure 8:
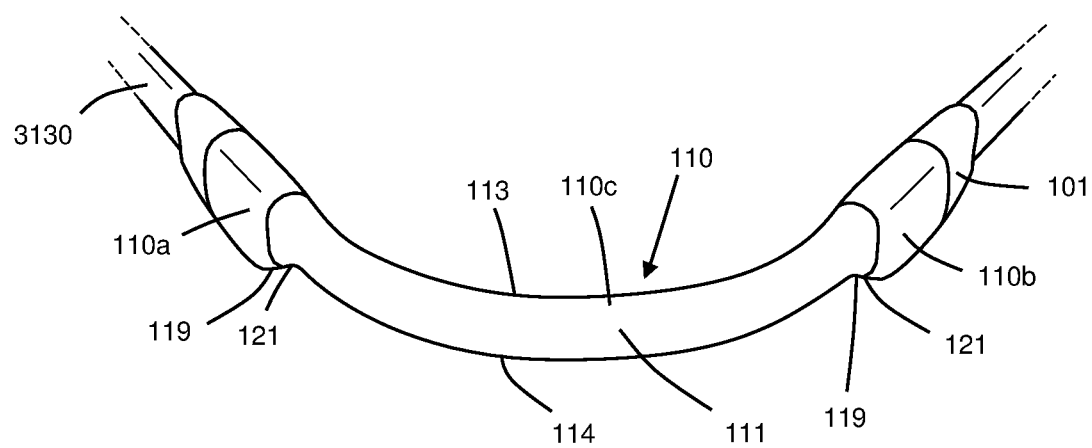
FIG. 8 is a front perspective view of the yoke and connector assembly of FIG. 7.

In one form, a washer box housing 102 is attached to each end of the yoke 100 and a headgear strap connector 3140 is attached to each washer box housing 102, as shown in FIGS. 7 and 8. Again, any suitable form of attachment may be used, such as a snap-fit arrangement, a magnetic connection, or over-moulding, for example.

The elastomeric yoke 100 may comprise a front surface 111, a rear surface 112, an upper surface 113, and a lower surface 114. The yoke may have a height defined by the distance between the upper surface and lower surface of the yoke and may have a length defined by the distance between opposing ends 115 of the yoke.

In one form, the yoke 100 may be angled or curved along its length and may comprise a middle region 110c located between two side regions 110a, 110b. In one form, the side regions 110a, 110b form a pair of arms extending from the middle region 110c and terminating at the distal ends of the yoke 100.

In one form, the cross-section of the yoke 100 may vary along its length. For example, in one form, the height of the middle region 110c of the yoke is less than the height of the side regions 110a, 110b of the yoke, to create a yoke with a thinner middle region 110c and flared ends 115. By providing a yoke with a thin middle region 110c, the height of the middle region 210c of the yoke channel 210 may be thinner, which provides additional space on the frame body 2210 in which to locate a larger gas inlet 2220 and optionally also an outlet vent 2200.

The elastomeric yoke 100 may be formed from any suitable material or combination of materials that allow the yoke to stretch and flex. For example, the yoke 100 may be formed from a rubberized material, silicone, or an elastomer.

The yoke 100 may be configured to engage with at least one retention member 220 on the frame 2200 of the patient interface 2000 to attach the yoke 100 to the frame.

In one form, the yoke may comprise one or more engagement members 120 and the frame may comprise one or more retention members 220 for engaging with the engagement member(s) of the yoke to hold the yoke 100 to the frame 2200. Typically, the engagement member 120 of the yoke 100 and the retention member 220 of the frame are configured to hold the yoke 100 under tension when the yoke 100 is attached to the frame 2200. The engagement members 120 and retention members 220 may take many different forms. Where the frame comprises a yoke channel, the yoke channel 210 may comprise one or more retention members 220 that are intended to prevent the yoke 100 from unintentionally disconnecting from the yoke channel 210

In one form, the walls 211, 212, 213 of the yoke channel 210 may act as retention members, such as by being shaped to form retention members, by retention the yoke 100 within the channel 210, such as under clamping or frictional forces. For example, the yoke 100, when in an unstretched form, may be dimensioned to have a greater height than the height of at least a portion of the channel 210. By stretching the yoke 100, the yoke body 110 becomes thinner and may be fitted within the channel 210. As the yoke 100 is released to its unstretched state, the height of the yoke increases again so that upper and lower surfaces 113, 114 of the yoke press against upper and lower surfaces 211, 212 of the channel to hold the yoke 100 within the channel 210 under clamping forces and/or frictional forces. The elastomeric material may provide additional grip or could be textured to provide even further grip.

Figure 9:
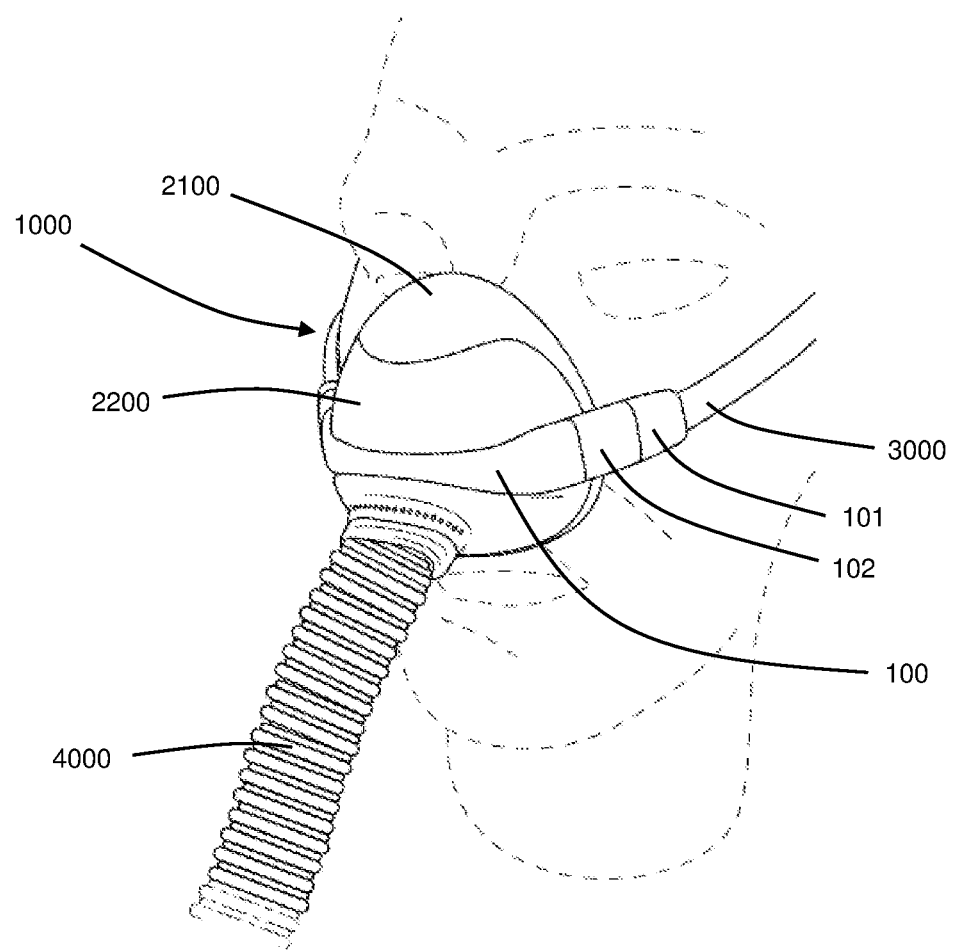
FIG. 9 is a perspective view of another form of yoke and frame in which the yoke is elastomeric and has rounded edges configured to fit within a yoke channel having a substantially 'C-shaped' cross-section.

In another form, as shown in FIGS. 9 and 10, the yoke 100 comprises rounded edges. The rounded edges may improve the aesthetic appeal of the yoke and improve the feel of the yoke in a patient's hand. The softer look and feel of a yoke with rounded edges may be particularly fitting and appealing in a bedroom environment. In this embodiment, a washer box housing 102 may be connected directly between the yoke 100 and a strap connector 101 at each end of the yoke, rather than being integrally formed at an end of the yoke. The strap connector 101 and washer box housing 102 may be formed separately from the yoke 100 and may be configured to attach together by any suitable attachment system, such as a snap-fit arrangement or over-moulding, for example. Both the yoke 100 and the strap connectors 101 are preferably made from an elastomeric material so that both of these parts are flexible and substantially soft to touch.

In one form, at least a portion of the yoke channel 210 has a substantially rounded 'C-shaped' cross-section configured to substantially correspond with a yoke 100 having substantially rounded edges. The 'C-shaped' profile of the channel 210 may extend substantially along the entire length of the channel 210 or may be provided at only the middle region 210c of the channel or only the side regions 210a, 210b of the channel. Preferably, the 'C-shaped profile' is provided in at least the middle region 210c of the channel. For example, as shown in FIG. 10, at least a portion of the yoke channel 210 may comprise a substantially 'C-shaped' cross-section in which the height of the opening 214 at the front of the channel $H_1$ is less than the maximum interior height $H_2$ of the yoke channel. In this configuration, edges of the upper and lower surfaces 211, 212 of the channel each form a lip to define the front opening 214 of the channel. The lips of the channel 210 project toward each other so that the distance between the lips is less than the maximum distance between the upper and lower surfaces 211, 212 of the channel. In a one form, the upper and lower surfaces 211, 212 of the channel are substantially concave along the length of the channel 210, so that the maximum distance between the upper and lower surfaces 211, 212 is found at the mid-point of the curve. In one form, at least the middle region 210c of the yoke channel comprises a substantially 'C-shaped' lateral cross-section with longitudinally concave upper and lower surfaces 211, 212. By providing a yoke channel 210 in which at least a portion of the yoke channel comprises a substantially 'C-shaped' lateral cross-section, it may be possible to improve the retention of a yoke 100, having a substantially 'C-shaped' lateral cross-section, within the yoke channel 210, due to the retention forces being applied to a larger surface area of the yoke, i.e. along the length of at least the middle region 210c of the yoke, rather than only at a shoulder 119 or abutment surface 121.

In its original state, the height of the yoke 100 (i.e. the maximum distance between the upper and lower surfaces of the yoke) is greater than the height $H_1$ of the channel opening 214, but may be less than, substantially the same, or slightly greater than the interior height $H_2$ of the channel 210. The elasticity of the stretchable/elastomeric yoke 100 means that the yoke may be stretched across the frame 2200 of the patient interface 2000 to become thinner in height so as to fit through the narrow front opening 214 of the yoke channel. When stretching the rounded yoke 100 across the frame 2200, the yoke may also be twisted slightly so that one of the upper or lower surfaces 113, 114 of the yoke enters the opening 214 of the yoke channel 210 first. This may reduce how much the yoke 100 needs to be stretched in order to fit through the opening 214. The yoke 100 is then pushed fully into the channel 210 and released so that the yoke returns to its original un-stretched state. The surfaces of the unstretched yoke 100 press against surfaces of the channel 210 to hold the yoke within the lipped channel until such time as the yoke 100 is stretched to become thinner and is then pulled out of the channel 210. In this way, walls 211, 212, 213 of the yoke channel 210 may act as retention members to hold the yoke 100 within the yoke channel 210.

Figure 11:
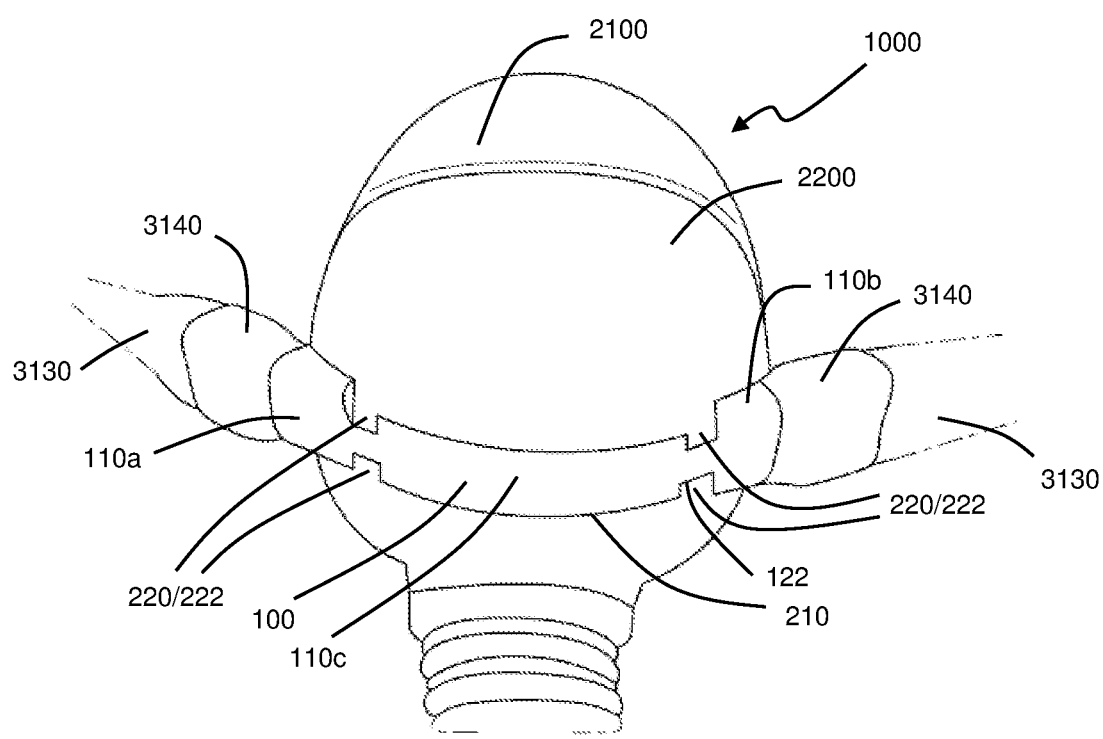
FIG. 11 is a front view of another form of yoke and frame, in which the frame comprises retention features in the form of tabs to hold the yoke within the yoke channel of the frame.
Figure 12:
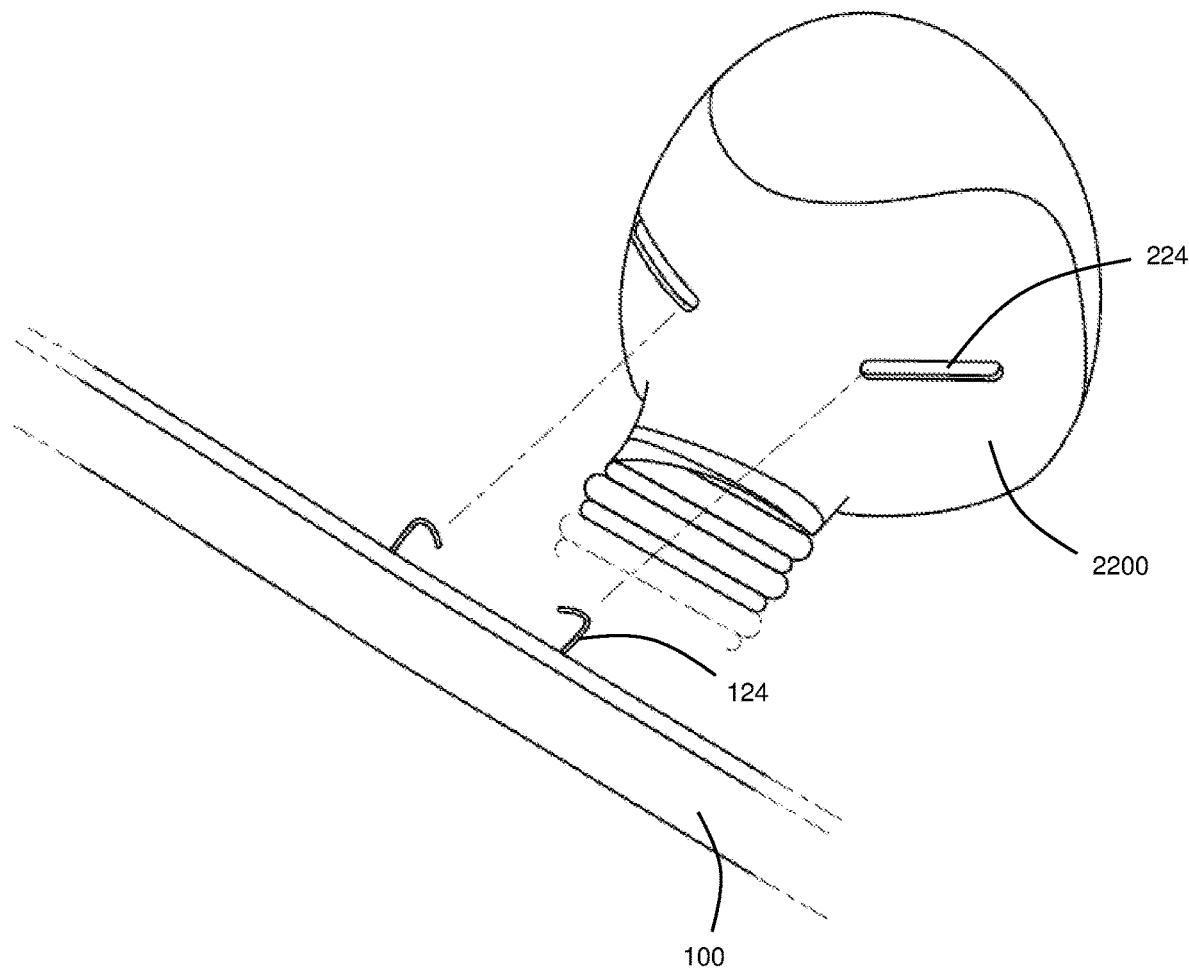
FIG. 12 is a perspective view of one form of yoke and frame in which the frame comprises retention members in the form of apertures and the yoke comprises engagement members in the form of projections or hooks configured to engage with the apertures of the frame to hold the yoke to the frame.

In another form, the frame 2200 may comprise at least one retention member 220 in the form of a projection 222 that is configured to engage with a recess 122 formed on the yoke 100 when the yoke is positioned within the yoke channel 210, as indicated in FIG. 11. Alternatively, the frame 2200 may comprise a retention member in the form of a recess 224 configured to engage with an engagement member in the form of a projection 124, such as an arm or hook for example, provided on the yoke 100 when the yoke is located on the frame, as shown in FIG. 12.

In yet another form, as indicated in FIG. 11, the yoke channel 210 may comprise retention members 220 in the form of projecting tabs 222 that at least partially project across the front opening 214 of the yoke channel to protrude over the front surface 111 of the yoke when the yoke is located within the channel 210.

Other suitable forms of retention members may be used to help secure the yoke within the yoke channel. For example, the yoke and frame may each comprise hooks configured to engage with each other.

Optionally, one or more walls 211, 212, 213 of the yoke channel 210 may be specially shaped to form a retention member 220, such as an abutment surface 221, that is configured to abut or engage with an engagement member 120, such as an abutment surface 121, of a yoke 100 to hold the yoke within the yoke channel 210.

For example, as shown in FIGS. 13 to 17, the yoke 100 may comprise at least one engagement member 120 in the form of an abutment surface 121 configured to clamp against a retention member 220 in the form of a corresponding abutment surface 221 of the frame. The yoke abutment surface 121 may generally face toward a virtual vertical line passing through the centre of the yoke 100 and may project from a rear and/or upper and/or lower surface 112, 113, 114 of the body 110 of the yoke. Similarly, the yoke channel 210 may comprise at least one complementary retention member in the form of an abutment surface 221, which faces generally away from a virtual vertical line passing through the centre of the channel 210 and that is provided on the rear and/or upper and/or lower walls 213, 211, 212 of the yoke channel 210 respectively.

In another form, at least one abutment surface may be located on the frame, but outside of the yoke channel, for pressing against a corresponding abutment surface of a yoke.

An abutment surface 121, 221 on the yoke and/or frame may be configured to help a user to locate the yoke 100 correctly within the yoke channel 210 of the frame. Optionally, an abutment surface on the yoke and/or frame 121, 221 may be configured to ensure that the yoke 100 is oriented the right way up within the yoke channel 210.

Preferably, the yoke 100 and frame 2200 each comprise a pair of abutment surfaces. 121, 221 For example, each side of the yoke 100 may comprise an abutment surface 121a, 121b, preferably at the side regions 110a, 110b of the yoke or at a transitional region between the middle 110c and side regions 110a, 110b. Similarly, each left and right side of the yoke channel 210 may comprise an abutment surface 221a, 221b, preferably at the side regions 210a 210b of the channel or at the transitional region between the middle 210c and side regions 210a, 210c.

Figure 13:
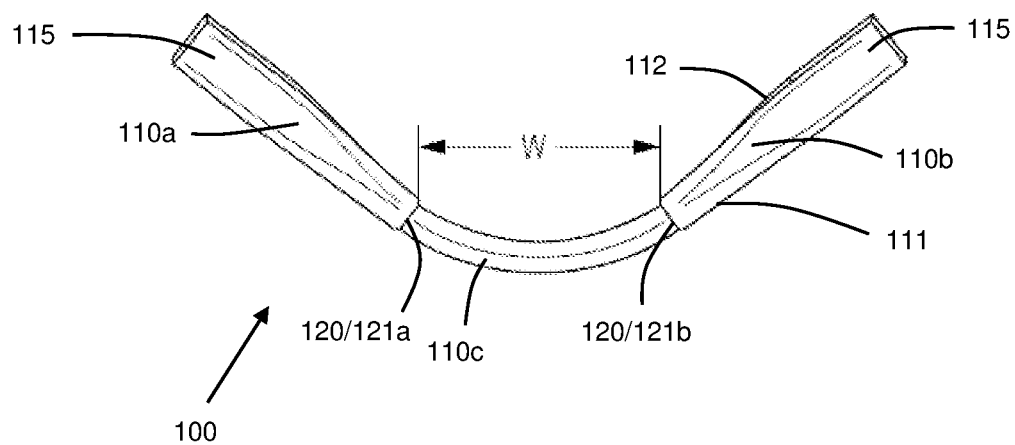
FIG. 13 is a top view of the yoke of FIG. 6 having a middle region located between two side regions and showing angled guiding surfaces at the transitional regions between the middle region and side regions.
Figure 14:
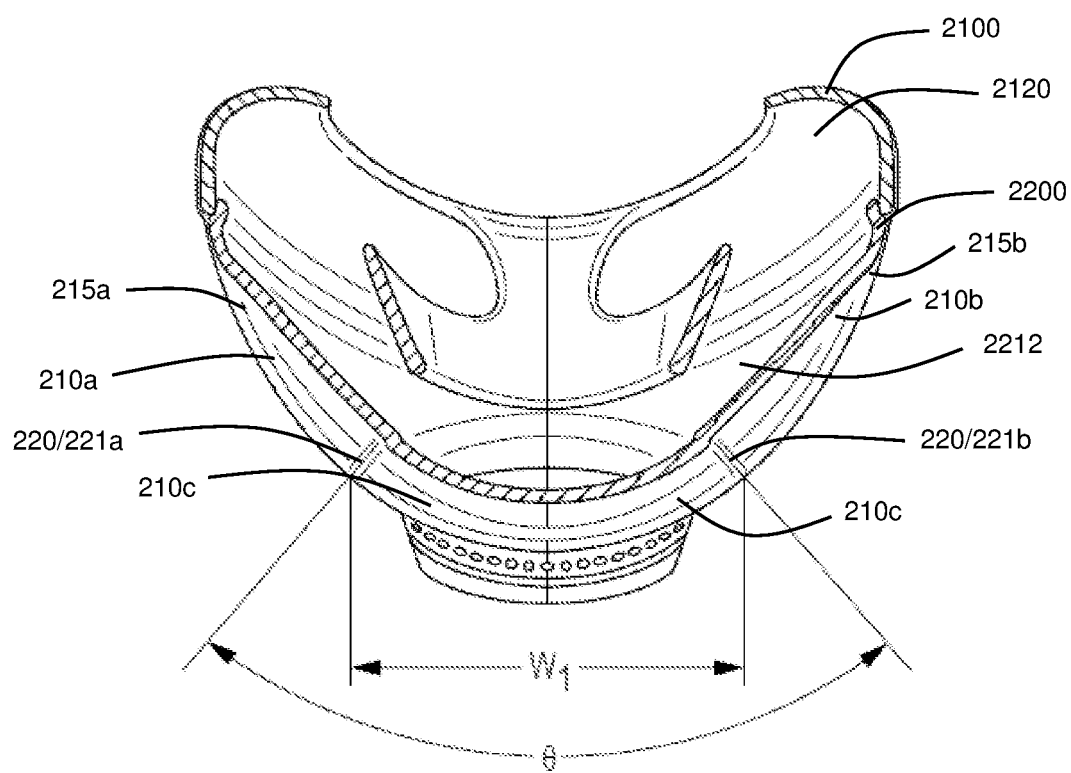
FIG. 14 is a cross-sectional view through line A-A of FIG. 5 and showing the frame having a curved channel with angled guiding surfaces to engage with the guiding surfaces of a corresponding yoke.
Figure 15:
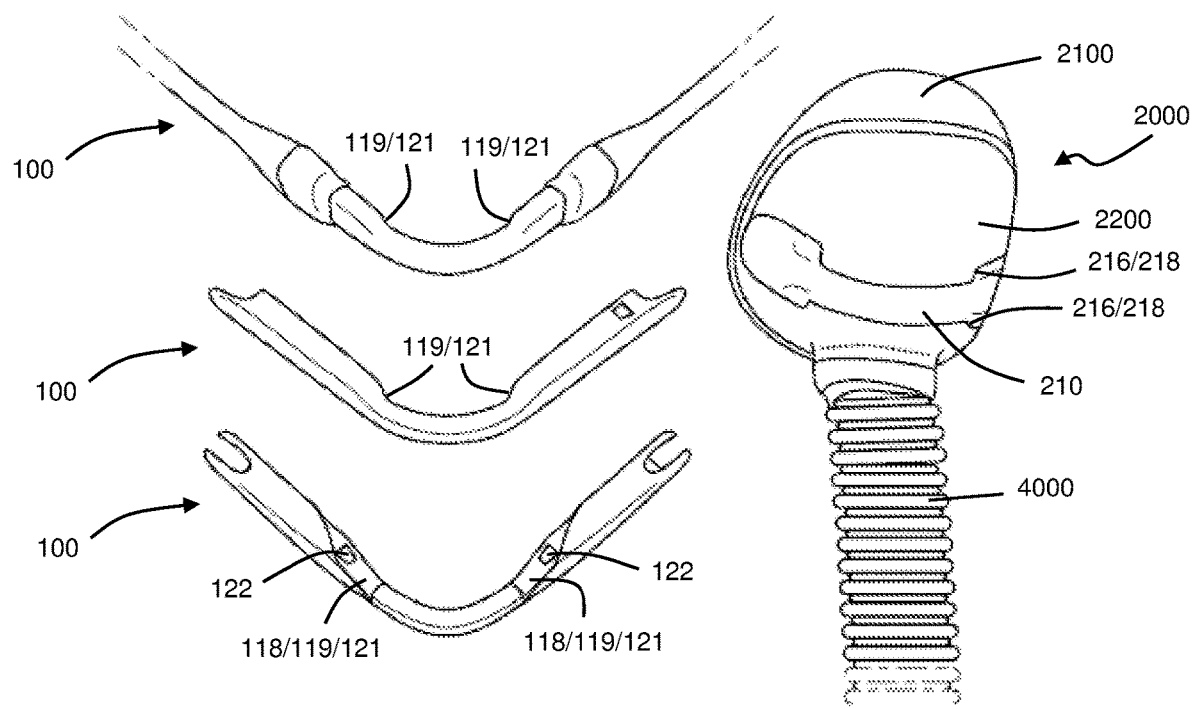
FIG. 15 is a top perspective view of various forms of yoke and one form of frame having a yoke channel with abutment surfaces to engage with a yoke having substantially corresponding abutment surfaces.

In one form, the yoke 100 may comprise a stepped profile so that the side regions 110a, 110b are larger than the middle region 110c, as shown in FIGS. 13 and 15. As shown in FIGS. 14 and 15, the yoke channel 210 of the frame 2200 may comprise a substantially corresponding stepped profile so that the side regions 210a, 210b of the yoke channel 210 are larger than the middle region 210c of the yoke channel 210. Preferably, each abutment surface 121, 221 is located at a transitional region between the middle region 110c, 210c and a side region 110a, 110b, 210a, 210b of the yoke 100 and of the yoke channel 210. For example, the upper surface 113 of each side region 110a, 110b of the yoke may comprise a step or shoulder 119 so that the height of middle region 110c of the yoke may be less than the height of the side regions 110a, 110b. Each step/shoulder 119 comprises a transitional surface between the middle 110c and adjacent side region 110a, 110b. The transitional surface may comprise a sloping or substantially perpendicular abutment surface 121 between the upper surface 113 of the middle region 110c and the upper surface 113 of the side region 110a, 110b.

Each abutment surface 121 of the yoke may be configured to substantially align with a corresponding abutment surface 221 of the yoke channel in the frame 2200. For example, the side regions 210a, 210b of the upper wall 211 of the yoke channel may comprise a correspondingly shaped stepped profile to form a step or shoulder 216 so that the height of the yoke channel 210 at the side regions 210a, 210b is greater than at the middle region 210c. Each step/shoulder 216 comprises a transitional surface between the middle 210c and adjacent side region 210a, 210b of the channel 210. The transitional surface may comprise a sloping or substantially perpendicular abutment surface 221. The abutment surfaces 121, 221 of the yoke and yoke channel should preferably substantially complement each other. Therefore, a sloping abutment surface 121 of the yoke should be configured to abut against a correspondingly sloped abutment surface 221 of the yoke channel. Similarly, a substantially perpendicular abutment surface 121 of the yoke should be configured to abut against a substantially perpendicular abutment surface 221 of the yoke channel.

In other forms, the lower or rear surface 114, 212 of the yoke and channel may have at least one stepped or sloping transitional surface to provide an abutment surface 121, 221, as described above.

In yet another form, the stepped or sloping transitional surface may extend from the lower surface 114, 212 around the upper 113, 211 and rear surfaces 112, 213 of the yoke and channel. Or the stepped of sloping transitional surface may be formed on the lower 114, 212 and rear surfaces 112, 213 of the yoke and channel; or on the lower 114, 212, rear 112, 213, and upper 113, 211 surfaces of the yoke and channel.

In one form, as shown in FIGS. 5, 7, 8, 13, 15, and 17, the upper and/or lower surface(s) 113, 114 of the yoke may be configured to provide a pair of abutment surfaces 121 that angle inwardly toward each other in a direction from the front surface 111 of the yoke toward the rear surface 112. As shown in FIGS. 4, 5, 14, 15, and 17, the abutment surfaces 221 of the yoke channel 210 may be correspondingly angled and located on the upper and/or lower surface(s) 211, 212 of the channel, as the case may be.

In this form, the minimum distance W between abutment surfaces 121 on the yoke should be less than the maximum distance $W_1$ between abutment surfaces 220 on the yoke channel or frame, as shown in FIGS. 13 and 14. In this configuration, to fit the yoke 100 within the yoke channel 210, the yoke 100 is stretched so that the middle region 110*c* of the yoke is longer than the middle region 210*c* of the channel. Once the stretched yoke 100 is fitted within the channel 210, the yoke may be released to its unstretched state. As the yoke 100 retracts to its unstretched state, the abutment surfaces 121 of the yoke retract towards and clamp against the abutment surfaces 221 of the yoke channel 210 under tension to hold the yoke in place within the channel 210.

As will be appreciated, the stepped or sloping profiles of the abutment surfaces 121, 221 of the yoke and yoke channel should substantially correspond in angle and location when the yoke 100 is fitted within the yoke channel 210.

The engagement member(s) 120 of the yoke and the retention member(s) 220 of the frame 2200 may each form a hinge point around which at least the ends of the yoke 100 can flex, so that when the yoke is attached to front straps 3130 of headgear, the angle of each front strap is conformable to the patient's physiology. For example, abutment surfaces 121, 221 of the yoke and yoke channel may each form a hinge point around which at least the ends of the yoke 100 can flex to form a comfortable respiratory mask system 1000 that sits well on the patient's face.

In some forms, the yoke 100 may be configured to provide one or more guides 118, such as guiding surfaces configured to about one or more corresponding guides, such as guiding surfaces 218 on the frame 210 in order to help a patient to locate the yoke 100 correctly on the frame 210. For example, the guiding surfaces 118, 218 may comprise tapered lead in surfaces on the yoke 100 and the yoke channel 210. In some forms, the guiding surfaces 118, 218 may also act as abutment surfaces 121/221 to help retain the yoke 100 within the yoke channel 210, as described above. For example, the yoke 100 may comprise one or more shoulders 119, as described above, and the yoke channel 210 may comprise a substantially corresponding profile. One or more surfaces of the shoulders 119 of the yoke and yoke channel may comprise guiding surfaces 118, 218 that may help a patient to guide the yoke to the correct location within the yoke channel.

In some embodiments, it may be preferred for the yoke and frame to each comprise at least two guiding surfaces—preferably one guiding surface at or near each side region of the yoke and of the frame.

Preferably, at least one guide/guiding surface 118 is provided on the rear and/or upper and/or lower surfaces 112, 113, 114 of the yoke. Similarly, at least one corresponding guide/guiding surface 218 may be provided on the rear and/or upper and/or lower walls 213, 211, 212 of the yoke channel. Additionally or alternatively, at least one guide/guiding surface may be located on the frame 2200, but outside of the yoke channel.

In one form, the yoke may comprise one or more projections that project from the rear and/or upper and/or lower surface of the yoke. The projection(s) may each comprise at least one guiding surface configured to abut a corresponding guiding surface of the frame.

The guiding surfaces 118 of the yoke 100 may be substantially perpendicular to an adjacent surface 112, 113, 114 of the yoke body 110 or may slope at an angle of between 0-90° from the adjacent surface. For example, where the guiding surface 118 is located on the upper surface 113 of the yoke, the guiding surface 118 may slope at an angle of between 0-90° with respect to the upper surface 113. Similarly, guiding surfaces 218 of the yoke channel 210 may be substantially perpendicular to an adjacent surface of the yoke channel or may slope at an angle of between 0-90° from an adjacent surface of the yoke channel 210.

In one form, an over-moulding may be located at or near each end 115 or side region 110*a*, 100*b* of the yoke. One or more edges of the over-moulding may form one or more guiding surfaces 118.

Whatever configuration of guides/guiding surfaces is used, the guiding surface(s) 118 of the yoke 100 preferably substantially correspond with the guiding surface(s) of the frame 2200 to correctly guide the yoke 100 into the yoke channel 210.

The guides/guiding surfaces 118, 218 provide an indicator that may help a patient to centre and align the yoke 100 correctly within the channel 210. The indication provided by the guiding surfaces 118 may be particularly useful where the guiding surfaces are provided on shoulders 119, 216 of a yoke and yoke channel that each have a substantially square stepped profile. This is because it is difficult for a patient to misalign the squared corners of the shoulders 119, 216. In some forms, the yoke 100 and channel 210 may be configured so that as the yoke 100 is fitted into the channel 210, contact between the guiding surfaces 118, 218 of the yoke and channel may provide tactile feedback to the patient that the yoke is correctly aligned and retained within the yoke channel.

Figure 17:
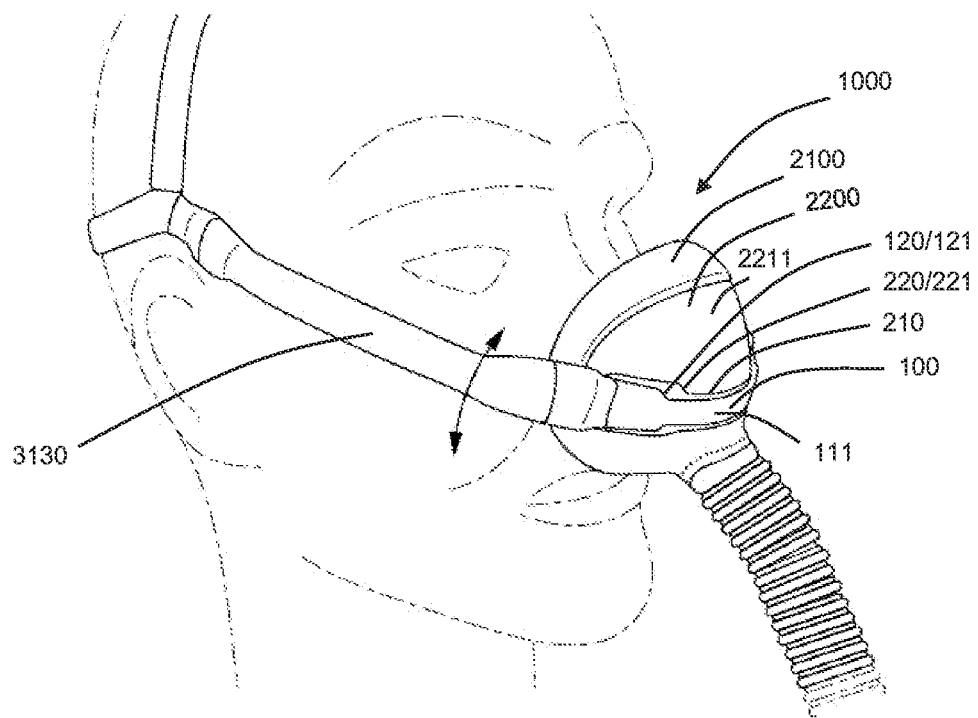
FIG. 17 is a side perspective view with arrows showing how the ends of the yoke of the invention may flex substantially vertically.

In one form, as shown in FIG. 17, the front surface 111 of the yoke is preferably smooth and may be configured to be substantially flush with the front surface 2211 of the frame when the yoke 100 is properly fitted within the yoke channel 210. In this configuration, the flush front surfaces 111, 2211 of the yoke and frame may provide a useful indication to a patient that the yoke 100 is correctly located within the channel 210.

In one form substantially the whole of the body of the elastomeric yoke 100 may be stretchable. In yet another form, only a portion of the yoke 100 is stretchable. For example, only a portion of the yoke 100 may be formed from an elastomeric material.

Figure 29:
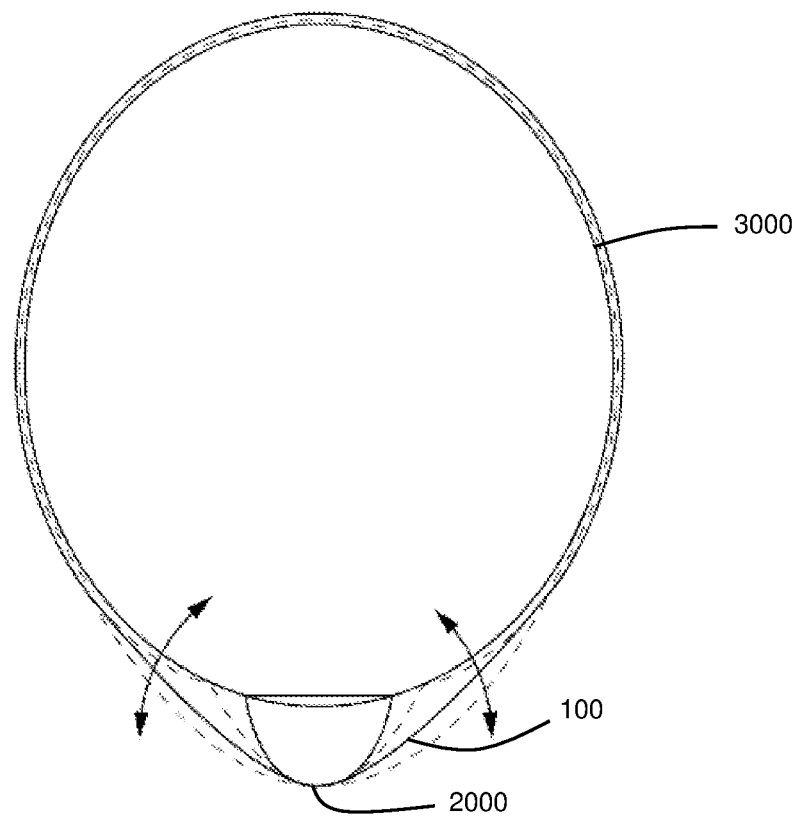
FIG. 29 is a schematic top view with arrows showing how the ends of the yoke of the invention may flex substantially horizontally.

In one form, as shown in FIG. 15, the yoke 100 comprises a stretchable middle region 110*c* comprising an elastomeric material and rigid or semi-rigid side regions 110*a*, 110*b*. In one form, at least portions of the side regions 110*a*, 110*b* of the yoke may be substantially rigid to provide extra stability to the yoke 100 and to enhance the engagement between the yoke 100 and frame 2200. The substantially rigid portions of the yoke may provide improved structure and stability to the front straps 3130 of the headgear, whilst maintaining flexibility due to the flexible nature of the connection with the elastomeric middle region 110*c*, which allows the angle of the front straps 3130 to be variable, as shown in FIGS. 17 and 29. In some forms, the side regions 110*a*, 110*b* may each comprise a washer box housing 102 to hold a washer mechanism to be used with an automatically adjustable headgear system 3000, as described above.

In one form, the substantially rigid portions of the yoke may be configured to provide haptic feedback that indicates to a patient that the yoke 100 is correctly fitted within the yoke channel 210. The haptic feedback may be in the form of a clicking noise or a tactile click or connection feeling, for example.

The elastomeric nature of the yoke 100 allows the yoke to be manipulated (such as by stretching the yoke longitudinally) to fit within the yoke channel 210 and to hold the yoke in place within the channel 210.

Figure 16A:
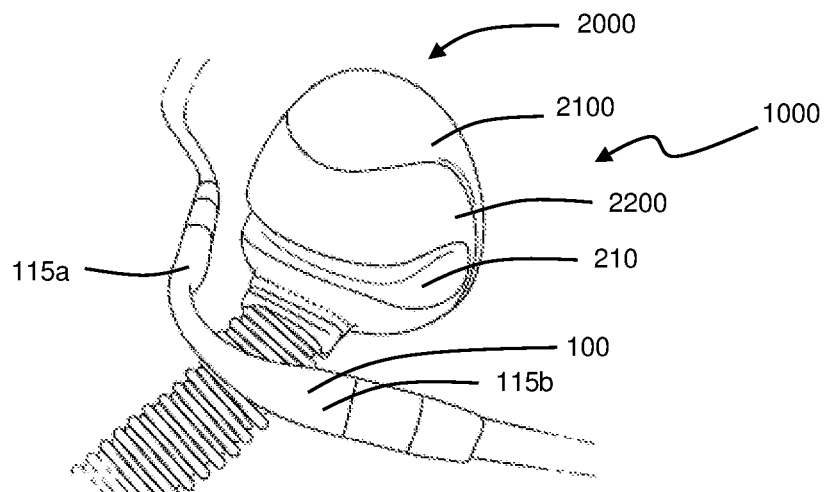
FIGS. 16A to 16C illustrate a method for fitting an elastomeric yoke within a yoke channel of a frame.
Figure 16B:
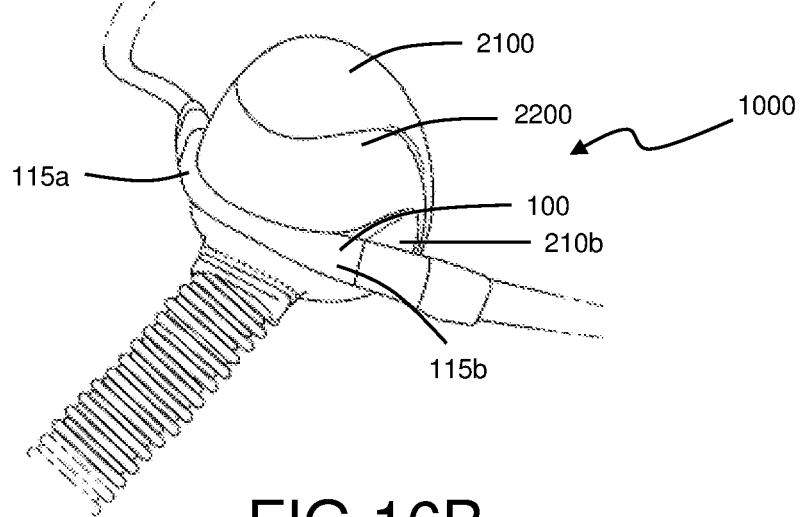
Figure 16C:
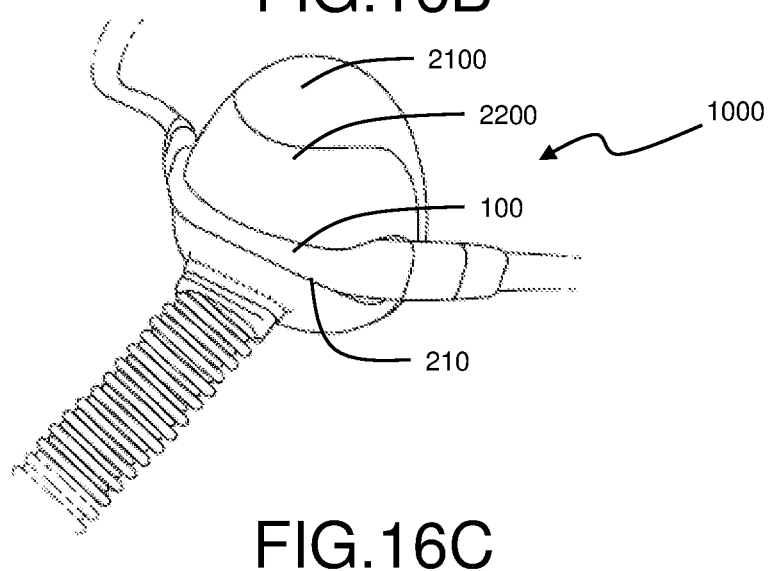

One process of fitting one form of elastomeric yoke 100 within a yoke channel 210 comprises the following steps, as shown in FIGS. 16A to 16C:

1. Press a first end 115a of the yoke 100 into the corresponding first end of the yoke channel 210. Where the yoke comprises shoulders 119 and abutment surfaces 121, which may be formed on the shoulders 119 of the yoke, the process of fitting an elastomeric yoke 100 within a yoke channel 210 may also comprise the step of aligning the first abutment surface 121a of the first shoulder 119a of the yoke into abutment with the first abutment surface 221 of the corresponding first shoulder 216a of the yoke channel 210. Frictional forces should now hold the first end of the yoke 100 within the channel 210, as shown in FIG. 16B.

2. Wrap the free second end 115b of the yoke 100 across the front opening of the yoke channel 210 to the other side of the frame 2200.

3. Pull the free second end 15b of the yoke 100 laterally away from the frame 2200 to stretch the yoke 100 so that the second abutment surface 121b of the yoke is closer to the second end of the yoke channel 210 than is the second abutment surface 221b of the yoke channel 210.

4. Press the second end 115b of the yoke 100 into the second end of the yoke channel 210 and release the yoke 100. As the yoke is released, tension on the yoke is reduced so that the yoke retracts and the second abutment surface 221b of the yoke 100 clamps against the second abutment surface 221b of the yoke channel 210, as shown in FIG. 16C.

The yoke 100 should now be held within the channel 210 to secure the frame 2200 to the headgear 3000. The free ends of the yoke 100 may project from the lateral ends 215a, 215b of the yoke channel 210 to attach to free ends of the headgear front straps 3130.

In at least one embodiment, one process of fitting an elastomeric yoke 100 within a yoke channel 210 comprises the following steps:

holding or pressing a first end 115a of the elastomeric yoke 100 to a corresponding first end 215a of the yoke channel 210;

applying tension to the yoke 100 to alter at least one dimension, shape, and/or configuration of the yoke, such as by stretching the yoke longitudinally for example;

placing or pressing the yoke 100 into a position in the yoke channel 210;

releasing the tension to engage the yoke 100 with a retention member 220, such as an abutment surface 221 or one or more walls of the yoke channel for example.

In at least one embodiment, the at least one dimension, shape, and/or configuration of the yoke 100 is a change in yoke cross-section or yoke length.

In at least one embodiment, the step of applying tension to the yoke 100 to alter at least one dimension, shape, and/or configuration of the yoke causes the length of the yoke to stretch and/or extend. In such an embodiment, a distance W between the first and second abutment surfaces 121a, 121b of the yoke 100 may be greater than a distance $W_1$ between the first and second abutment surfaces 221a, 221b of the yoke channel 210.

In at least one embodiment, the step of releasing the tension on the yoke 100 causes the yoke to retract or reduce in length such that the second abutment surface 121b of the yoke abuts with the second abutment surface 221b of the yoke channel 210. In at least some configurations the first and second abutment surfaces 121a, 121b of the tensioned yoke apply a compressive force to the first and second abutment surfaces 221a, 221b of the yoke channel 210, such that the yoke 100 is retained within the yoke channel 210.

In at least one embodiment, the yoke channel 210 comprises a 'C-shaped' cross-section. The step of applying tension to the yoke 100 to alter at least one dimension, shape, and/or configuration of the yoke reduces a height of the yoke 100 to be the same or less than a height $H_1$ of the yoke channel opening 214 of the 'C-shaped' cross-section.

In at least one embodiment, the step of applying tension to the yoke 100 to alter at least one dimension, shape, and/or configuration of the yoke allows the yoke to pass through the yoke channel opening 214, when under tension.

In at least one embodiment, the step of releasing the tension on the yoke 100 to engage the yoke with a retention member 220 causes the height of the previously stretched yoke 100 to return to its original state, such that upper and lower surfaces 113, 114 of the yoke then press against upper and lower surfaces 211, 212 of the yoke channel to retain the yoke 100 within the yoke channel 210.

In another embodiment, as shown in FIGS. 18 to 27, the elastomeric yoke 100 may comprise a body 110 that comprises an elongate strip comprising elastomeric material. The yoke may be at least partially, and preferably fully, formed of elastomeric material so that the elastomeric portion of the yoke 100 may be configured to stretch longitudinally along its length. In some forms, the elastomeric portion of the yoke 100 may also be configured to stretch laterally along its height.

The yoke 100 may also comprise at least engagement member 120 in the form of a yoke aperture 125 formed within the body 110 of the yoke 100. Each yoke aperture 125 may pass through the yoke 100 from the front surface 111 to the rear surface 112 of the yoke or to a midpoint or a point between the front and rear surfaces 111, 112 of a multi-layered yoke, such as a two layered yoke.

One or more yoke apertures 125 may be formed in the yoke using any suitable method, such as by using a hole punch to form the yoke aperture(s), by laser cutting or blade cutting the aperture(s), or by 3-dimensionally knitting the yoke to form one or more apertures 125 in the yoke, for example.

Figure 21:
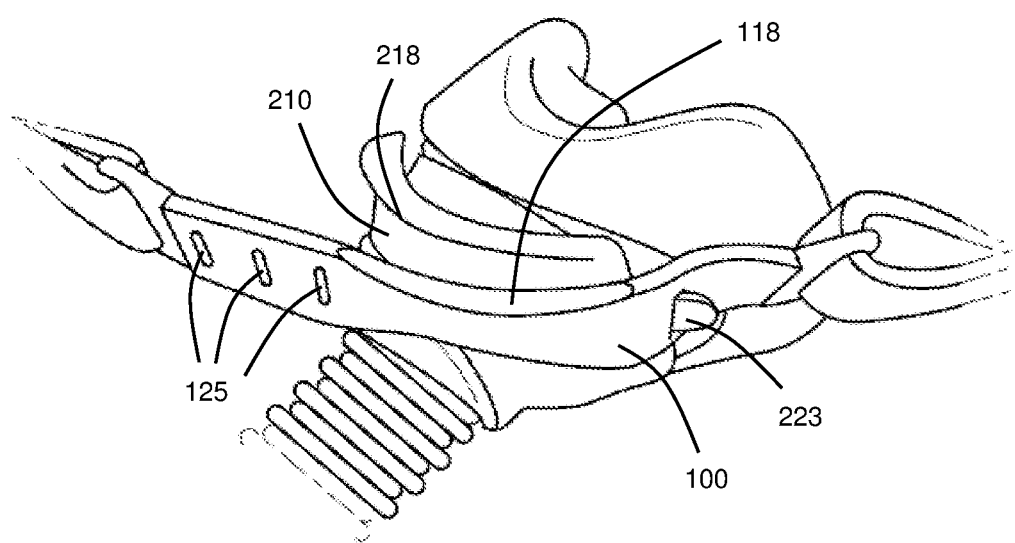
FIG. 21 is a perspective view of an adjustable yoke and frame assembly in which the yoke provides an adjustment system to provide a comfortable fit for a user.

Each yoke aperture 125 is configured to receive a retention member 220 of a frame 2200 of a patient interface 2000. The retention member 220 may be a projecting arm 223, such as a post, anchor point, or hook for example, that projects from the frame and that is configured to be at least partially received within the yoke aperture 125. The frame may comprise a single retention member 223 for engagement with a single yoke aperture 125. Alternatively, the frame 2200 may comprise two or more retention members 223 for engagement with two or more yoke apertures 125. In yet another form, the yoke 100 may provide an adjustable fit by comprising multiple yoke apertures 125 for engagement with one or more retention members 223 of the frame, as shown in FIG. 21.

Each yoke aperture 125 is configured to be placed over a projecting arm 223 of the frame 2200, so that at least a portion of the arm 223 is held within the yoke aperture 125. Preferably, the arm 223 extends through the yoke aperture 125 to project from the front surface 111 of the yoke.

In one form, the patient interface 2000 may comprise a pair of arms 223 projecting from left and right sides of the frame 2200 and the yoke 100 may comprise at least a pair of apertures 125. The distance between the apertures 125 may be less than the distance between the arms 223 so that when the yoke is attached to the frame by placing the arms 223 through the apertures 125, the yoke is held to the frame under tension.

For example, FIGS. 18 to 21 show one form of respiratory mask system 1000 comprising an elastomeric yoke 100 comprising at least a pair yoke apertures 125 for engagement with a pair of projecting arms 223 provided on a frame 2200 of a patient interface 2000. In this form, the yoke 100 has a substantially elongate shape and is configured to stretch along its length when under tension. A yoke aperture 125 is provided on each side region 110a, 110b of the yoke 100.

In one form, the frame 2200 may comprise a yoke channel 210 located on the front surface 2211 of the frame body 2210. An arm 223 may project from each end 215a, 215b of the yoke channel 210. Preferably, each arm 223 comprises rounded ends to help guide the arms 223 through respective yoke apertures 125 without catching or tearing at the yoke. This configuration is especially useful where the yoke is formed from a stretchy fabric.

The yoke 100 is configured to be at least partially located within the yoke channel 210 so that the upper and lower surfaces 211, 212 of the yoke channel 210 may abut or lie adjacent to the respective upper and lower surfaces 113, 114 of the yoke. The yoke channel 210 helps prevent the yoke 100 from slipping upwards or downwards on the frame 2200. In this way, the yoke 100 can be located substantially centrally on the frame to help prevent skewing of the yoke relative to the frame 2200.

In another form, the yoke may be configured to press against the front surface of the frame and to be held to the frame under tension, without the frame necessarily comprising a yoke channel.

The yoke 100 of FIGS. 18 and 20A to 20C comprises a pair of yoke apertures 125, one located at each side region 110a, 110b of the yoke so that the yoke apertures 125 lie proximate to the projecting arms 223 when the yoke is positioned alongside the yoke channel 210. In one form, as shown in FIG. 20A, each yoke aperture 125 is in the form of a slot and each arm 223 is in the form of a thin tab for projecting through a corresponding yoke aperture/slot 125 of the yoke 100.

A method of attaching the yoke 100 to the frame 2200 is shown in FIGS. 20A to 20C. As a first step, the yoke 100 is positioned proximate to the front surface 2211 of the frame. One end of the yoke 100 is then attached to the frame by pulling the yoke over the frame and over the first arm 223a, so that the first arm 223a projects through the first yoke aperture 125a, as shown in FIG. 20B. The elastomeric yoke is then stretched along its length and pulled across the frame 2200 and yoke channel 210 to align the second arm 223b with the second yoke aperture 125b. The tension of the yoke 100 is then released to at least some extent to allow the second arm 223b to project through the second yoke aperture 125b. The yoke is now attached to the frame, as shown in FIG. 20C. Preferably, the middle region of the yoke 100 that lies between the yoke apertures 125a, 125b remains slightly stretched and under tension as the yoke 100 is held against the frame 2200. In this way, the yoke 100 is pulled taught across the frame 2200 to create a snug fit and to hold the patient interface 2000 against a patient's face.

The retention members/arms 223 and yoke apertures 125 may be provided at any suitable location on the frame 2200 that allows the yoke 100 to attach to the frame 2200 in a stable position and to hold the yoke under tension. For example, a pair of yoke apertures may be provided in the middle region of the yoke for attaching to corresponding arms 223 provided on a middle region of the yoke channel 210 or the frame 2200.

Figure 27:
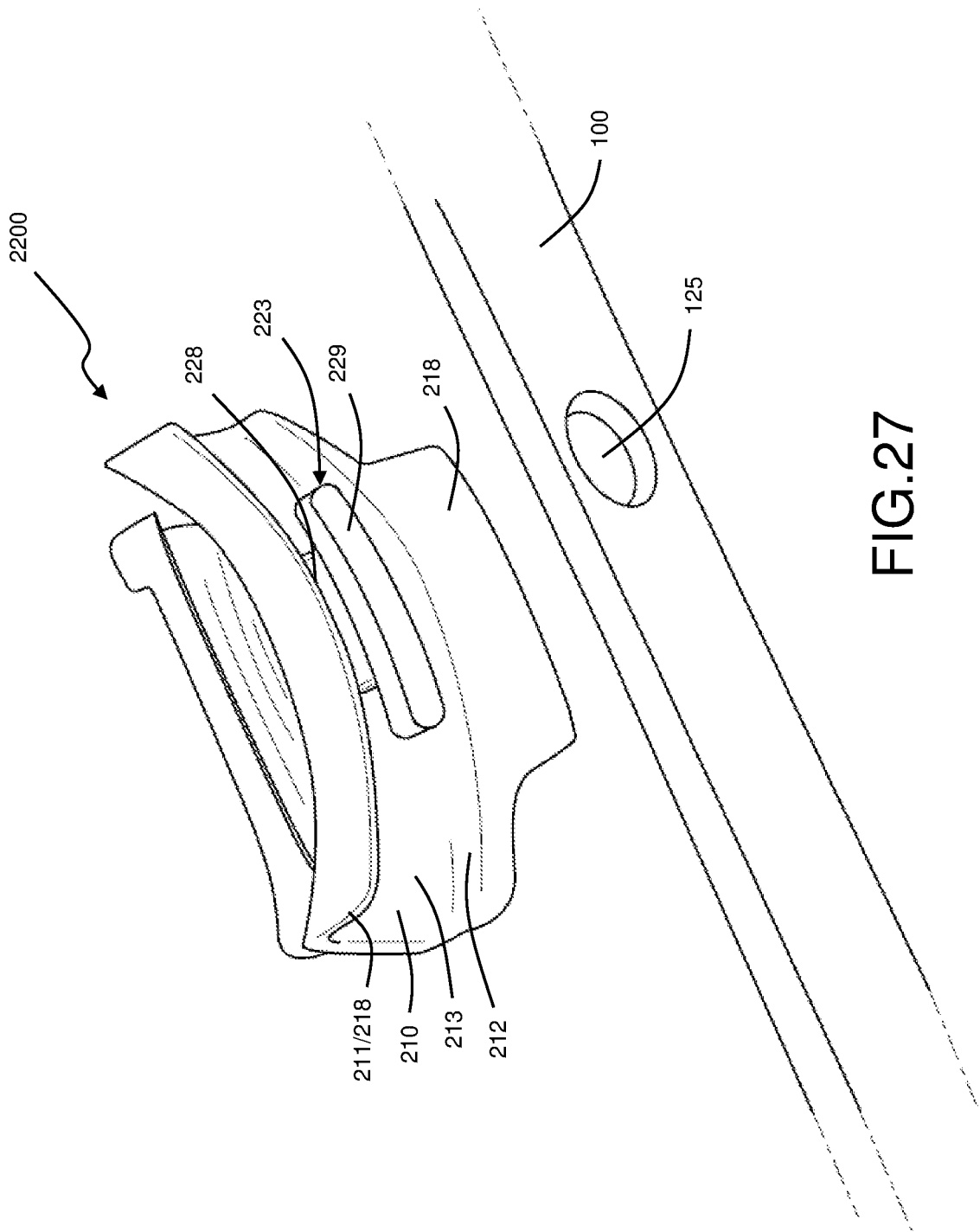
FIG. 27 shows yet another form of frame assembly to which an elastomeric yoke may be attached, this frame assembly comprising a single retention member or arm for engaging with an aperture of the yoke.

In some forms, as shown in FIG. 27, the lower wall 212 of the yoke channel 210 may comprise a guide 218 that forms a tongue extending downwardly from the yoke channel 210. The guide 218 helps a user to correctly locate the yoke 100 in the yoke channel 210 by encouraging the yoke 100 to slide upward and into the channel 210. Once the yoke 100 is in the correct position within the channel 210, the upper wall 211 of the yoke channel prevents the yoke 100 from sliding further up the frame 2200.

Figure 18:
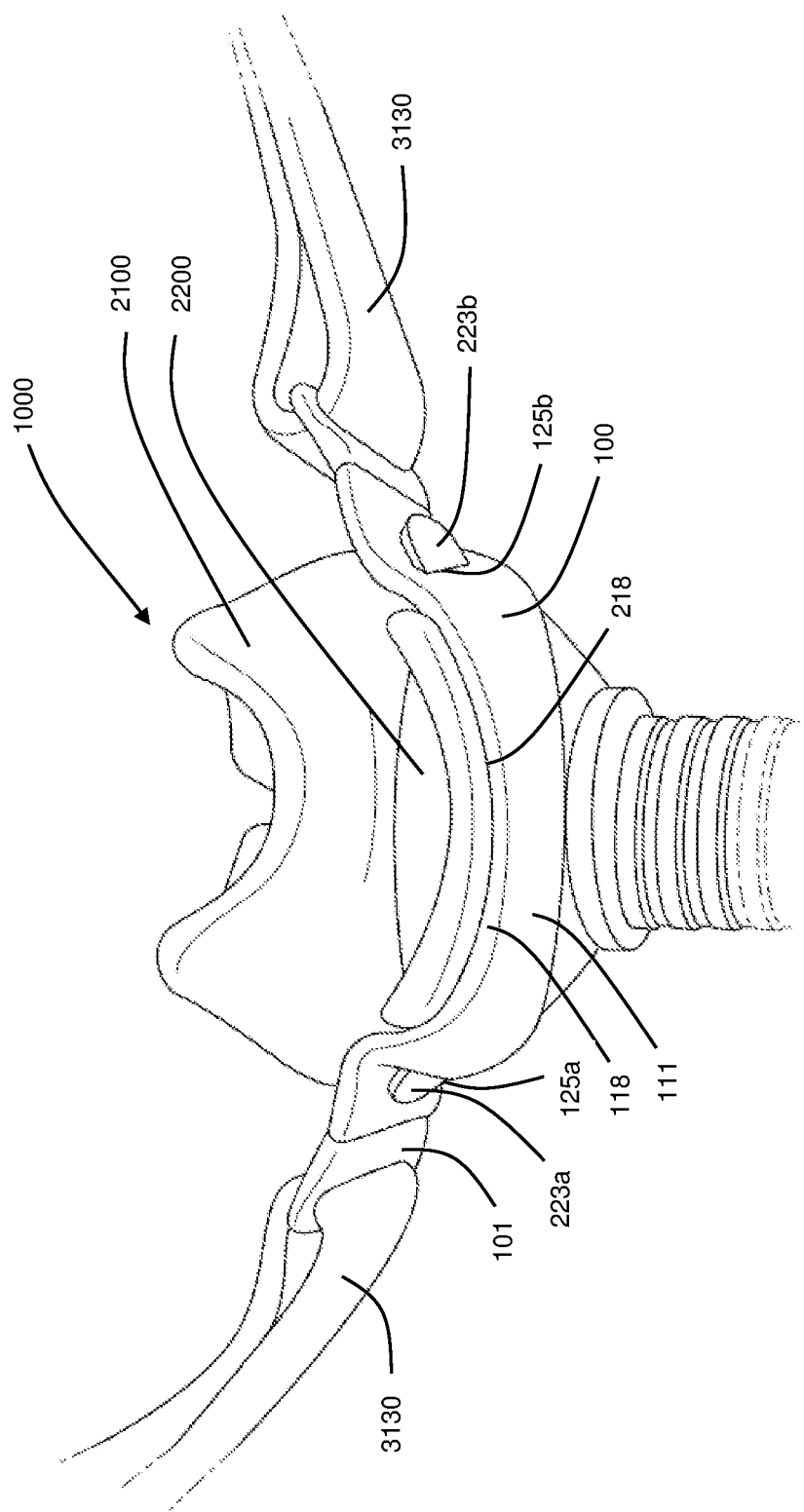
FIG. 18 is a front perspective view of yet another form of elastomeric yoke attached to one form of frame assembly.
Figure 19:
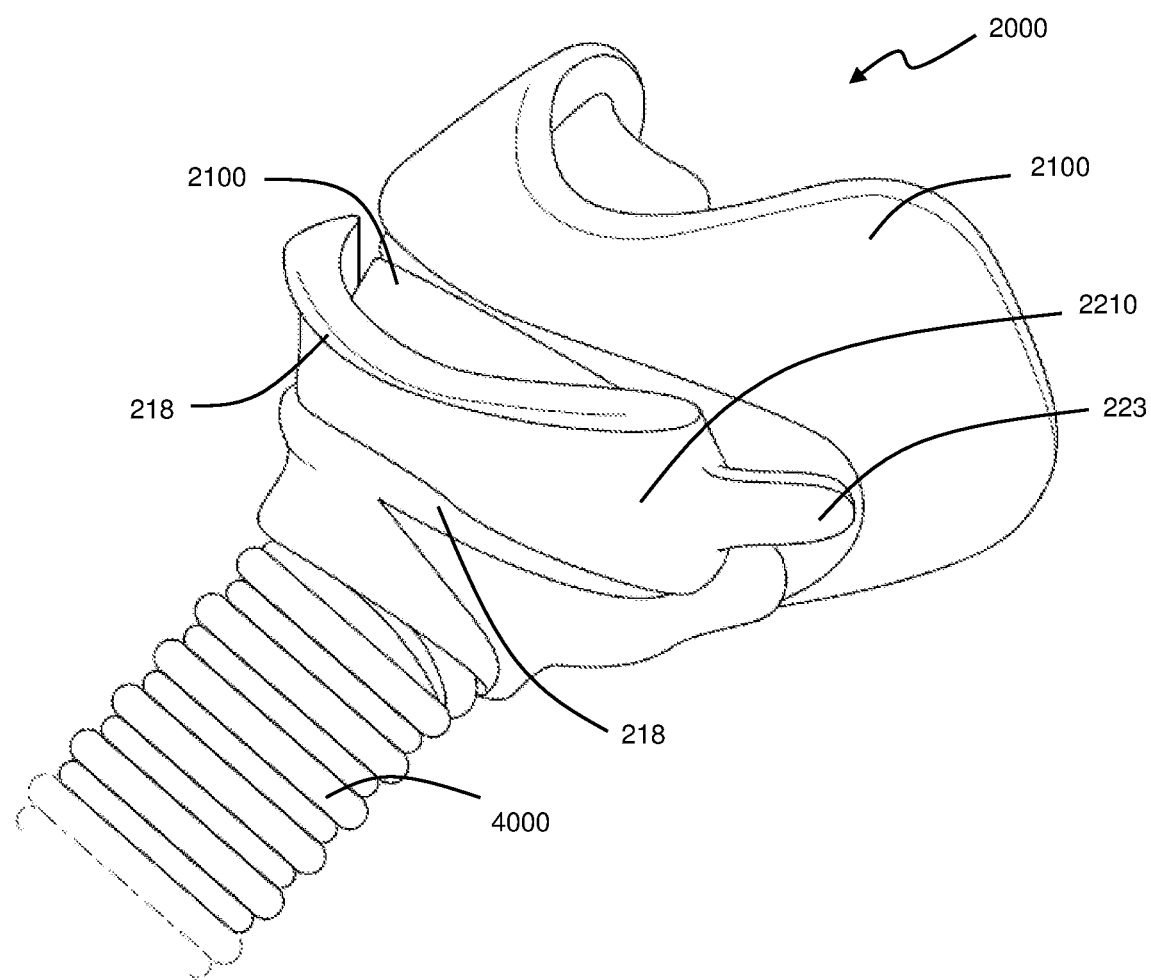
FIG. 19 is a side perspective view of the frame assembly of FIG. 18.
Figure 20:
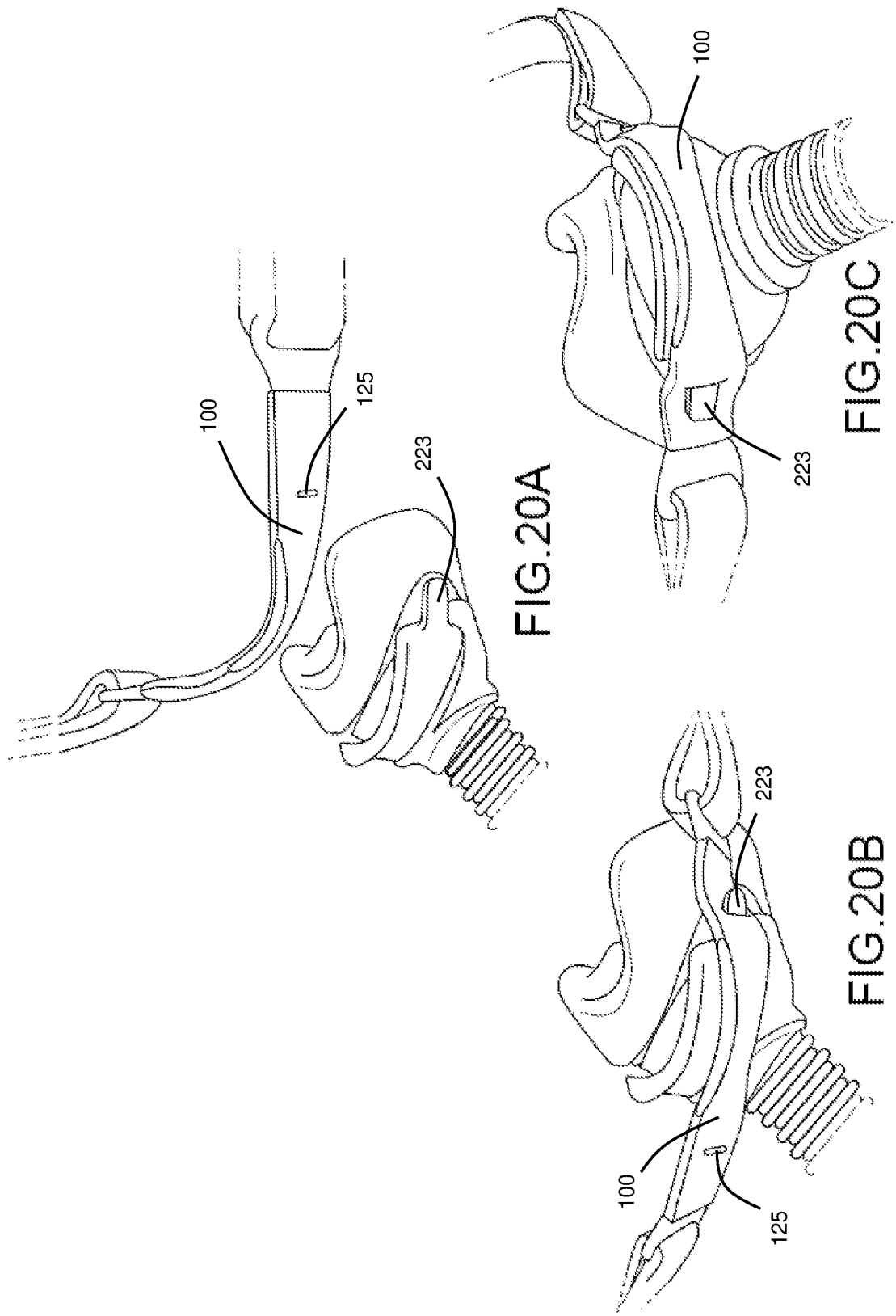
FIGS. 20A to 20C show a method of attaching the elastomeric yoke of FIG. 18 to the frame assembly of FIGS. 18 and 19.
Figure 22:
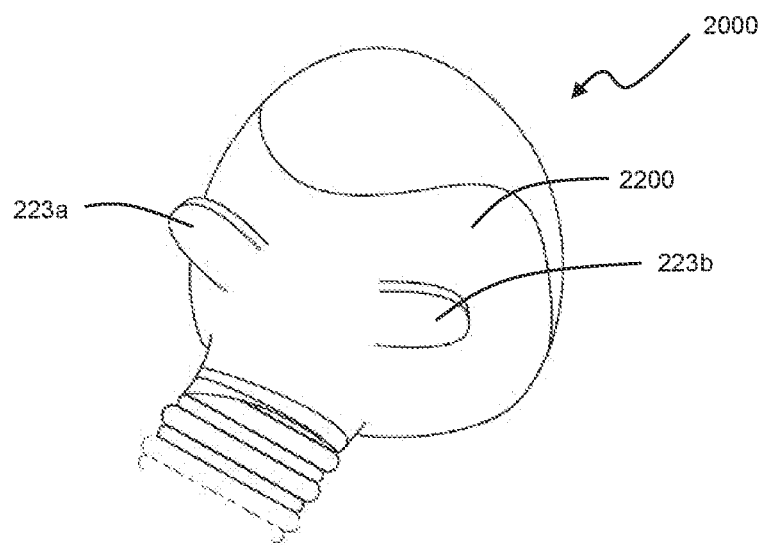
FIG. 22 is a perspective view of another form of frame for attaching to a yoke.
Figure 23:
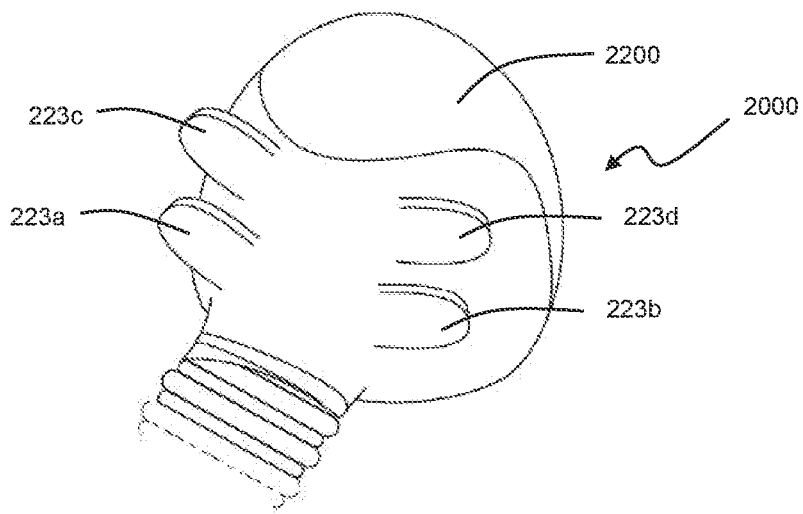
FIG. 23 is a perspective view of yet another form of frame that provides an adjustment system for attaching to a yoke.

In some forms, it is not necessary for the frame of the patient interface to include a yoke channel within which a yoke may be held. The yoke 100 may alternatively be attached to retention members 220 formed on the front surface of the frame. For example, arms 223 may project from the front surface 2211 of the frame 2200 at any suitable location. Preferably, the arms 223 and corresponding yoke apertures 125 of the yoke are configured to hold the yoke under tension when the yoke is engaged with the arms. In one form, as shown in FIG. 22, at least one arm 223 projects from opposing left and right sides of the frame 2200. In other forms, two or more arms 223 may project from the left and right sides of the frame 2200. For example, FIG. 23 shows a frame 2200 comprising a first pair of lower retention members/arms 223a, 223b projecting from the left and right sides of a frame 2200. The frame 2200 also comprises a second pair of upper retention members/arm 223c, 223d located above the lower arms 223a, 223b and projecting from each of the left and right sides of the frame 2200. In this form, a corresponding yoke may comprise a pair of upper and lower yoke apertures 125. In this form, two yoke apertures are positioned on each of the left and right side regions 110a, 110b of the yoke, one aperture above the other, to engage with arms 223a, 223b on the respective left and right sides of the frame. Alternatively, the yoke 100 may have at least one engagement aperture 125 located at each side region of the yoke, as shown in FIGS. 18 and 21. Each aperture 125 may be selectively engaged with one of the lower pair of arms 223a, 223b or one of the upper pair of arms 223c, 223d. In this configuration, the yoke and frame provide an adjustable fit for the user.

In both forms, the yoke 100 may be attached to the frame 2200 by engaging the yoke aperture(s) 125 on one side region of the yoke with the arm(s) 223 on a corresponding side of the frame, then stretching the yoke along its length to align the other yoke aperture(s) on the other side region of the yoke with the other arm(s) on the other side of the frame, before fitting the other arm(s) through the selected other yoke aperture(s) before releasing the yoke, as indicated in FIGS. 20A to 20C.

Where the yoke 100 comprises a series of yoke apertures 125, extending along at least a portion of the length of the yoke, and a frame 2200 comprises one or more arms 223, as shown in FIG. 21, a user may select which yoke apertures to engage with the arm(s) in order to adjust the yoke to provide a comfortable fit.

Figure 24:
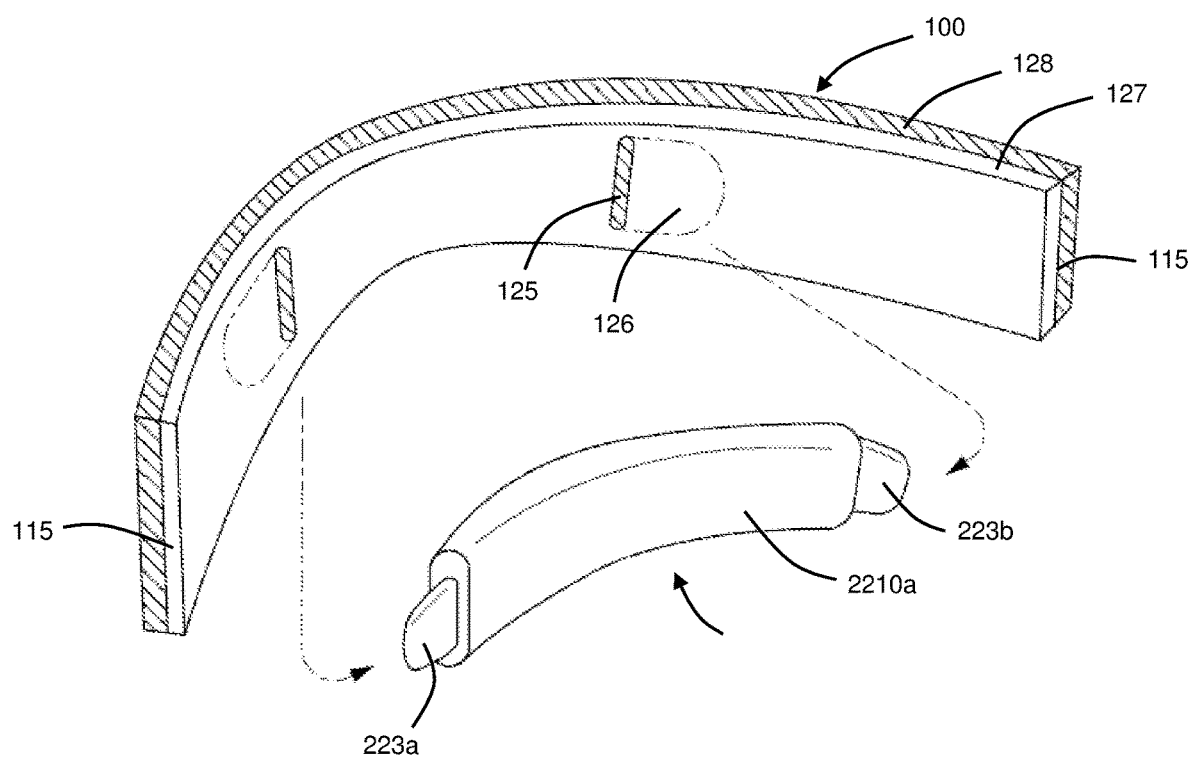
FIG. 24 shows a portion of one form of frame assembly and a portion of a yoke having pockets for engaging with retention members or arms of the frame.
Figures 25, 26:
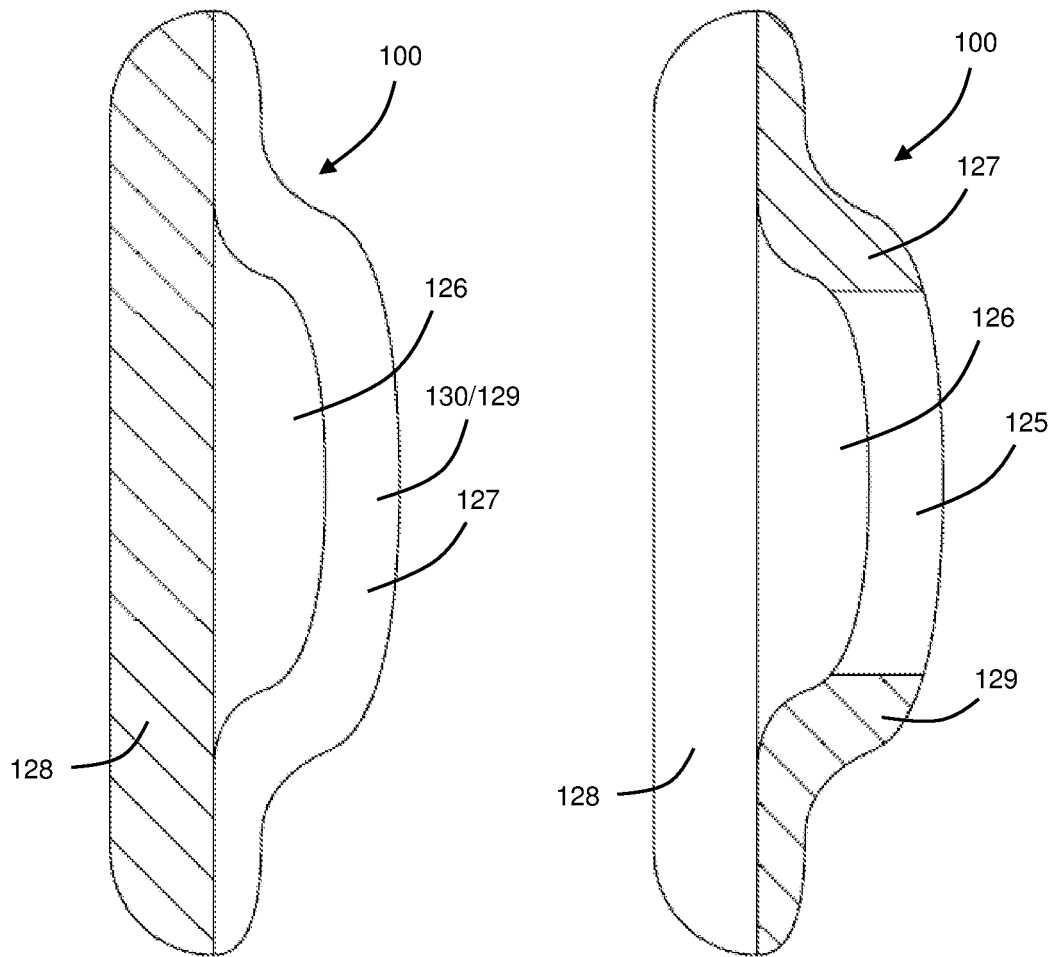
FIG. 25 is a schematic cross-sectional view of one form of elastomeric yoke having a pocket or loop for receiving a portion of a frame within the pocket or loop.
FIG. 26 is a cross-sectional view of another form of elastomeric yoke having at least one pocket formed between two layers of fabric and showing a yoke aperture formed in a first layer of fabric to allow a retention member to access the opening to the pocket.

FIGS. 24 to 26 show a portion of a frame body 2210a and alternative forms of yoke comprising engagement members/ yoke apertures 125 configured to engage with retention members/arms 223 of the frame to attach the yoke 100 to the frame 2200. In these forms, the yoke comprises at least one pocket or loop and preferably at least two pockets or loops 129 for receiving and engaging with one or more arms 223 of the frame.

In the embodiments shown in FIGS. 24 and 26, the yoke 100 comprises a multi-layered elastomeric body. Preferably, as shown, the yoke comprises two layers of fabric 127, 128 that extend substantially along the length of the yoke. However, in other forms the yoke may comprise there or more layers of fabric. The yoke 100 also comprises a pair of apertures 125, one of the apertures 125 being located on each side region 110*a*, 110*b* of the yoke. Each aperture 125 provides access to a pocket 129 provided on the yoke 100. The pocket 129 is formed by an opening 126 that exists between the layers of fabric 127, 128. For example, where the yoke 100 comprises two layers of fabric, a first inner layer 127 of fabric may include yoke apertures 125 that allow access to an opening 126 formed between the first layer 127 and a second, outer layer 128 of fabric. Where the yoke comprises three or more layers of fabric, the yoke apertures may be formed in only the inner layer to provide access to a pocket opening between the inner layer and an adjacent layer, or the yoke apertures may be formed through two or more layers of fabric to provide access to a pocket opening between deeper layers of the yoke. In these forms, the fabric layers preferably extend substantially along the length of the yoke.

In another form, only some regions, such as the side regions, of the yoke may comprise multiple layers of fabric. Preferably, two layers of fabric are provided at each side region 110*a*, 100*b*. For example, in the embodiment shown in FIG. 25, the yoke 100 may comprise a first layer 128 of elastomeric fabric that substantially extends across the length of the yoke. A second, inner layer 127 of fabric is provided at each side region 110*a*, 110*b* of the yoke so that each side region comprises two layers of fabric. A space or opening 126 is provided between the two layers 127, 128 at each side region 110*a*, 110*b*. Each opening 126 can be accessed by at least one yoke aperture 125, which may be formed through the inner layer of fabric. In another form, as shown, the yoke aperture 125 may be provided at an inside edge of the inner layer 127 of fabric. For example, an opening 126 may be formed between the two layers 127, 128 at the point near the middle region 110*c* of the yoke where the inner layer 127 terminates. This opening 126 may be created by stitching, bonding, welding or otherwise attaching upper and lower edges of the two fabric layers 127, 128 together but not attaching the inside edge of the inner fabric layer 127 to the other fabric layer 128. Other forms of creating a yoke aperture 125 at the edge of each inner layer may alternatively be used, such as 3-dimensionally knitting the yoke to have two or more layers of fabric 127, 128 at the side regions 110*a*, 110*b*. The yoke apertures 125 provide access to the inner openings 126 to form pockets 129 within the yoke.

In yet another form, as indicated by FIG. 25, the yoke 100 may comprise two or more layers of fabric 127, 128 at two or more locations along the length of the yoke. In this form, the yoke 100 may comprise a first layer of fabric 128 that substantially extends along the length of the yoke. Loops 130 of a second layer of fabric 127 may also be provided at the side regions 110*a*, 110*b* or along the length of the yoke 100. For example, the yoke may comprise a pair of loops 130, one at each side region 110*a*, 110*b* of the yoke. Alternatively, the yoke 100 may comprise two or more loops 130 at each side region 110*a*, 110*b* or multiple loops 130 extending across the length of the yoke 100 to provide multiple attachments points/anchor points to engage with one or more retention members 223 to allow for an adjustable fit. As above, inner edges of the loops 130 may provide yoke apertures 125 that provide access to an opening between the looped fabric 127 and the first fabric layer 128. The loops 130 act in a similar way to a pocket 129 in that each loop may receive and hold a retention member 223 between two layers of fabric 127, 128.

Each pocket 129 or loop 130 is configured to receive a corresponding retention member 223 within the pocket/loop. In this form, the yoke may be attached to a frame that does or does not comprise a yoke channel. The fabric layers may be made of the same material or different materials. For example, the inner layer of fabric may be softer than the outer layer to provide greater comfort to a user.

The pockets 129/loops 130 may be formed by any suitable method. In one form, the yoke 100 may be 3-dimensionally knitted to include pockets or loops. In another form, the yoke 100 may include an inner layer 127 and an outer layer 128 of material joined together, such as by bonding, welding, stitching, fusing, or otherwise. The yoke apertures 125 may be formed in the inner layer 127 and a pocket may be formed between the inner and outer layers 127, 128. Each pocket 129 may comprise an open area between the inner and outer layers 127, 128 of the yoke 100, as shown in FIGS. 24 to 26. The open area may be located next to a respective yoke aperture 125 and between that yoke aperture and an end 115 of the yoke.

In each of these embodiments, the frame and yoke may be dimensioned so that the middle region of the yoke (i.e. the region between the retention members) is held under tension when the yoke is attached to the frame. The tensile force helps to hold the yoke in position against the frame. To achieve this, the yoke apertures may be spaced at a distance from each other that is less than the distance between the retention members/arms.

One method of attaching the yoke to a patient interface is for a user to position a first engagement member, located at or near a first end of the yoke, adjacent to a first retention member on the patient interface, such as on the frame of a mask assembly. The first retention member may be located on a first side of the patient interface, such as on the left side for example. The first retention member is caused to engage with the first engagement member to hold the yoke to the patient interface at a first anchor point. The user then stretches the yoke along its length by pulling against the first anchor point until a second engagement member, located at or near the opposing to second end of the yoke, substantially aligns with a second retention member located on a second side, such as the right side, of the patient interface. The second engagement member is then caused to engage with the second retention member as the yoke is held under tension. The yoke is then released to at least partially release tension on the yoke. However, the yoke preferably remains under at least some tension to help hold the yoke to the patient interface.

In a more specific example of a method of attaching a yoke to a patient interface, a user pushes one end of a first retention member/arm 223 into a first yoke aperture 125 to hook the arm 223 around the yoke aperture and form a first anchor point. The user then stretches and deforms the yoke to place the yoke under tension as the user fits a second yoke aperture 125 around the other/second retention member 223. The user then releases the yoke to release at least some of the tension on the yoke. Where the distances between the yoke apertures of the yoke, when unstretched in its natural state, is less than the distance between first and second retention members on opposing left and right sides of the patient interface, the yoke will remain under tension while it is attached to the patient interface. The tension in the yoke helps to hold the yoke firmly in position against the patient interface.

In yet another form, the frame 2200 may comprise a single retention member 220. Preferably, the retention member forms a projecting arm 223 that is substantially centrally located on the front surface 2211 of the frame body 2210. A corresponding yoke 100 may comprise an engagement member in the form of a yoke aperture 125 that is substantially centrally located along the length of the yoke 100. The frame 2200 may or may not comprise a yoke channel 210 within which to receive the yoke 100.

Figure 28A:
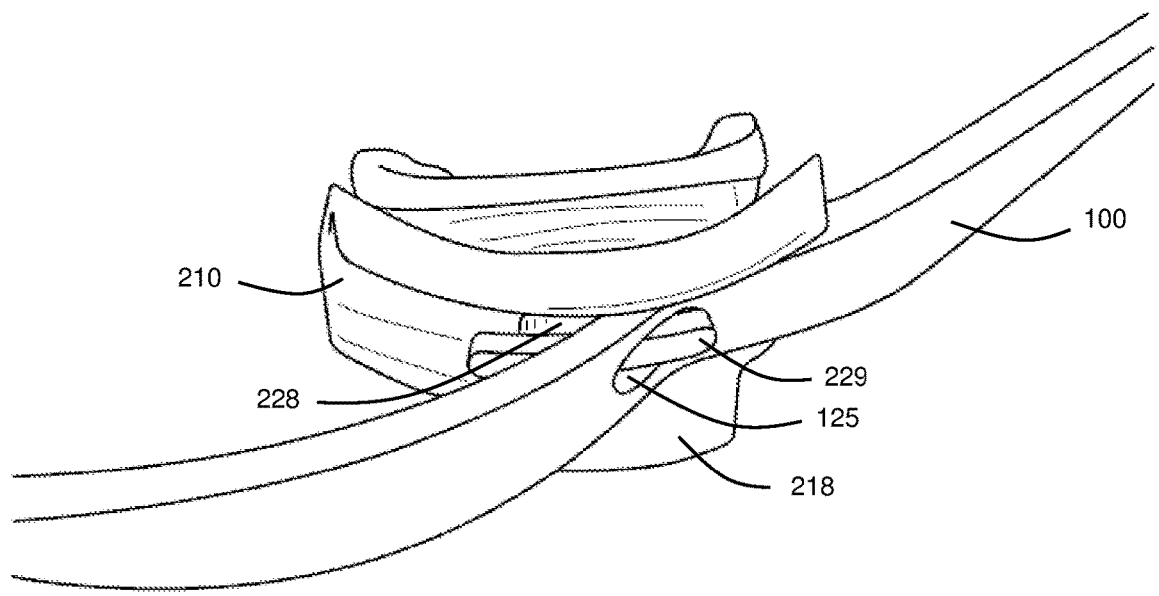
FIGS. 28A and 28B show a method of attaching the elastomeric yoke of FIG. 27 to the frame of FIG. 27.
Figure 28B:
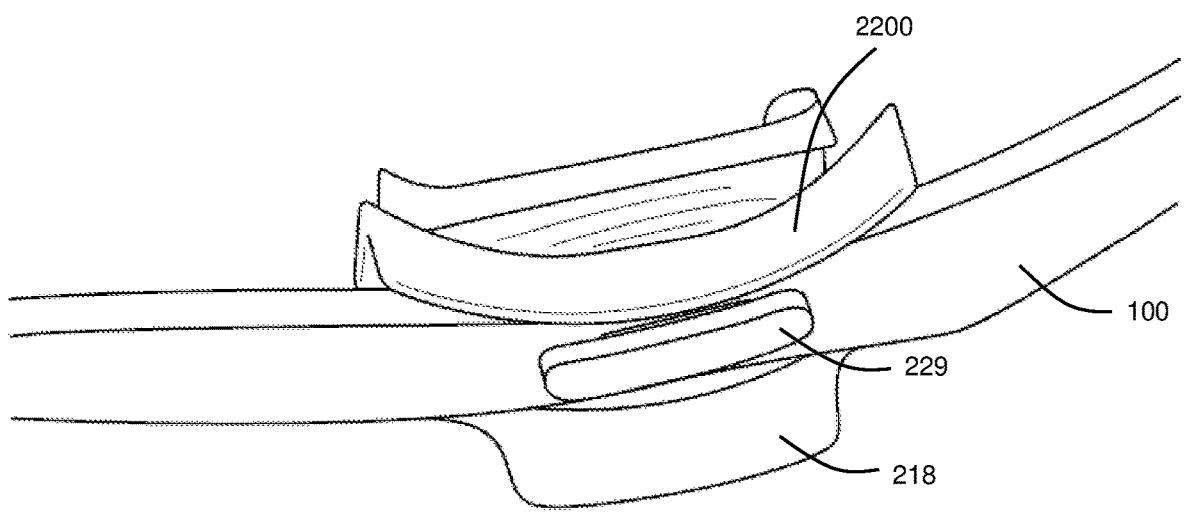

For example, as shown in FIGS. 27, 28A, and 28B, the frame may comprise a yoke channel 210 having an upper surface 211, a lower surface 212, and a rear surface 213, as described above. A retention member 223, such as an arm, anchor point, or post for example, may project from the rear surface 213 at the middle region of the yoke channel 210. The retention member/arm 223 may comprise a stem 228 and a capped distal end 229 that is wider, longer, or both wider and longer than the stem 228. For example, the distal end 229 of the arm 223 may comprise a peripheral flange that projects outwardly beyond the periphery of the stem 228. In one form, the arm 223 has a width that extends along a portion of the length of the yoke channel 210 to provide the arm with a substantially elongate width, as shown in FIG. 27. In another form, the arm 223 may be a mushroom shape or any other suitable shape for engaging with a yoke aperture 125.

An elastomeric yoke 100 having a substantially centrally located yoke aperture 125 may be provided for attachment to the frame 2200, as shown in FIG. 27. The yoke 100 may be configured to stretch along its length so that the yoke aperture 125 may be fitted over the capped end of the arm 223 so as to hold the stem of the arm 223 within the yoke aperture 125.

FIGS. 28A and 28B show a method of attaching a yoke 100 to a patient interface. In this method, a user positions the engagement member of the yoke adjacent to the retention member on the patient interface, such as on the frame of a mask assembly. The user then hooks the engagement member around the retention member to hold the yoke in place.

More specifically, a user may push one end of the elongate retention member/arm 223 into the yoke aperture 125 to hook the arm around the yoke aperture and form a first anchor point. The user then stretches and deforms the yoke to place the yoke under tension as the user stretches the yoke aperture 125 to reach around the other end of the elongate retention member 223. The user then releases the yoke to release at least some of the tension on the yoke. The yoke is caused to substantially revert toward its natural, unstretched state during which the yoke aperture 125 is smaller than the capped end 229 of the arm 223 and is therefore unable to disengage from the arm 223 without being stretched and pulled over the capped end 229.

In other forms, the yoke may attach to other regions of the patient interface. For example, the yoke may attach to one or more retention members of the seal of a patient interface.

The elastomeric material of the yoke 100 allows the yoke to flex substantially horizontally and/or substantially vertically. For example, the yoke 100 may flex towards or away from the frame body 2210 and the patient's face. Correspondingly, the yoke 100 allows the connection between headgear 3000 and the frame 2200 to be flexible so that the ends of the front straps 3130 can be flexed towards or away from each other. The broken lines in FIG. 29 illustrate how the ends 115 of the yoke 100 may flex substantially horizontally and the arrow on FIG. 17 indicates how the ends 115 of the yoke may flex in a substantially vertical direction. Each side of the yoke 100 can flex independent of the other side so that a force applied to one side is isolated from the other side. This means that the yoke 100 may be particularly suitable for patients lying on their side because one side of the yoke 100 may flex, when being pressed against a pillow for example, without breaking the seal between the frame seal 2100 and the patient's face.

The flexible nature of the elastomeric yoke 100 also allows the yoke to conform to different face shapes and widths. For example, the ends 115 of the yoke may be flexible or may be directly or indirectly attached to flexible elastomeric connectors 101, 3140 so that the ends 115 of the yoke or a yoke and connector assembly may flex toward or away from each other, or up and down relative to the middle region 110c of the yoke. This flexibility prevents the yoke ends 115 or the connectors 101, 3140 from digging into a patient's face.

The flexible yoke 100 may also improve the stability of the patient interface 2000 on a patient's face. For example, where a yoke 100 comprises projecting rigid ends 115 and the ends of the yoke become caught on bedding, a bending moment may result and may cause the patient interface 2000 to rotate on the patient's face. By providing a flexible yoke 100, the ends 115 of the yoke may flex and move independently of the middle region 110c of the yoke. Therefore, even if the yoke ends 115 become entangled in bedding, the flexible nature of the yoke 100 allows the patient interface 2000 to stay in the desired position on the patient's face The elastomeric yoke 100 may also be relatively simple to connect to the frame 2200. For example, if the respiratory mask system comprises a yoke 100 and a frame 2200 having a yoke channel 210 for receiving the yoke, the yoke 100 and yoke channel 210 may be configured to provide a patient with tactile or haptic feedback when the yoke 100 is correctly fitted within the channel 210.

The soft touch of the elastomeric material of the yoke 100 may also make the yoke 100 and headgear 3000 more comfortable to handle and may allude to the wash-ability of the headgear as a whole.

The elastomeric yoke allows the headgear assembly of the respiratory system to be easily removed from the patient interface/mask assembly without needing to laboriously disconnect components of the headgear assembly and mask assembly. In some forms, a user can detach the yoke and headgear from the mask assembly with one hand. Once detached, the yoke and headgear assembly may be washed. Where the yoke and headgear are made fully from fabric, the headgear assembly with yoke may be washed easily without concern for delicate non-fabric components.

The simplistic nature of the elastomeric yoke of the invention provides headgear bearing the yoke with a minimalist, uncomplicated aesthetically pleasing appearance. The headgear may also be lightweight.

The invention claimed is:

1. A headgear assembly for a patient interface of a respiratory system, wherein the headgear assembly comprises:
  at least one strap to wrap around a user's head; and
  a yoke connected to ends of the at least one strap, the yoke
    comprising a middle region located between two side regions that terminate at distal ends of the yoke, the two side regions of the yoke are substantially rigid;

wherein the yoke is at least partially formed from an elastomeric material and wherein the yoke comprises a first engagement member and a second engagement member, the first engagement member configured to engage with a first retention member of the patient interface, the second engagement member configured to engage with a second retention member of the patient interface, each of the first engagement member and the second engagement member is in the form of an aperture located in respective side regions of the yoke, wherein the yoke comprises a front surface and a rear surface, and wherein each aperture in the yoke passes through the yoke from the front surface to the rear surface.

2. The headgear assembly of claim 1, wherein the at least one strap comprises a rear strap connected to a pair of front straps, and wherein the distal ends of the yoke are configured to connect to free ends of the front straps.

3. The headgear assembly of claim 1, wherein the yoke is fully formed from an elastomeric material.

4. The headgear assembly of claim 1, wherein the yoke comprises an upper surface, a lower surface, a front surface and a rear surface, and wherein a pair of stepped regions are provided on the upper surface and/or lower surface and/or rear surface of the yoke, each stepped region separating the middle region of the yoke from each side region of the yoke.

5. The headgear assembly of claim 4, wherein each stepped region comprises a transitional wall separating the middle region from one of the two side regions, wherein each transitional wall forms an abutment surface configured to align with a corresponding abutment surface within a channel of a frame of the patient interface.

6. The headgear assembly of claim 5, wherein the abutment surfaces face toward each other and are angled outwardly toward the distal ends of the yoke.

7. The headgear assembly of claim 1, wherein each side region of the yoke comprises a washer box housing.

8. The headgear assembly of claim 7, wherein the headgear assembly comprises a directional lock, wherein the directional lock comprises at least one collection chamber to receive one or more filaments.

9. The headgear assembly of claim 1, wherein each distal end of the yoke is connected to a headgear connector assembly comprising a washer box housing and a connector configured to connect to a front strap of the at least one strap.

10. The headgear assembly of claim 1, wherein each distal end of the yoke is connected to a connector configured to connect to a front strap of the at least one strap.

11. The headgear assembly of claim 1, wherein the yoke comprises substantially rounded edges.

12. A respiratory system comprising:
a patient interface comprising a mask assembly; and
the headgear assembly of claim 1.

13. The respiratory system of claim 12, wherein each of the first retention member and the second retention member of the patient interface comprises an arm configured to be received within the respective aperture.

14. The respiratory system of claim 12, wherein the mask assembly comprises a seal and a frame, and wherein the frame comprises a front surface and a rear surface, the front surface of the frame comprising a yoke channel extending laterally across the frame, the yoke channel being configured to receive the yoke of the headgear assembly.

15. The respiratory system of claim 14, wherein the yoke channel comprises an upper surface, a lower surface and a rear surface, wherein edges of the upper and lower surfaces each form a lip to define a front opening of the yoke channel, and wherein the lips of the yoke channel project toward each other so that a maximum distance between the lips is less than a maximum distance between the upper and lower surfaces of the yoke channel.

16. The respiratory system of claim 15, wherein the upper and lower surfaces of the yoke channel are substantially concave along at least a portion of a length of the yoke channel to provide the yoke channel with a substantially C-shaped cross-section.

17. The respiratory system of claim 14, wherein the yoke channel comprises the first retention member and the second retention member configured to retain the yoke within the yoke channel.

18. The respiratory system of claim 17, wherein each of the first retention member and the second retention member comprises a tab that at least partially projects across the yoke channel and in front of the yoke when the yoke is located within the yoke channel.

19. The respiratory system of claim 12, wherein the mask assembly comprises a frame comprising a front surface and a rear surface, and wherein the first retention member and the second retention member project from the front surface of the frame for engagement with the first engagement member and the second engagement member of the yoke.

20. The respiratory system of claim 12, wherein the mask assembly comprises a frame comprising the first retention member and the second retention member in the form of a pair of arms projecting from left and right sides of the frame, and wherein a distance between the apertures is less than a distance between the arms.

* * * * *